US010085858B2

(12) United States Patent
Nelson

(10) Patent No.: US 10,085,858 B2
(45) Date of Patent: Oct. 2, 2018

(54) CARBON FIBER PROSTHETIC FOOT WITH HOLLOW CROSS SECTIONS

(71) Applicant: Ronald Harry Nelson, Salt Lake City, UT (US)

(72) Inventor: Ronald Harry Nelson, Salt Lake City, UT (US)

( * ) Notice: Subject to any disclaimer, the term of this patent is extended or adjusted under 35 U.S.C. 154(b) by 0 days.

(21) Appl. No.: 15/400,006

(22) Filed: Jan. 6, 2017

(65) Prior Publication Data
US 2017/0296362 A1    Oct. 19, 2017

Related U.S. Application Data

(63) Continuation of application No. 14/679,207, filed on Apr. 6, 2015, which is a continuation of application No. 13/686,652, filed on Nov. 27, 2012, which is a continuation of application No. 12/557,900, filed on Sep. 11, 2009, which is a continuation of application No. PCT/US2008/003394, filed on Mar. 13, 2008.

(60) Provisional application No. 60/906,687, filed on Mar. 13, 2007.

(51) Int. Cl.
*A61F 2/66*    (2006.01)
*A61F 2/50*    (2006.01)

(52) U.S. Cl.
CPC ........ *A61F 2/66* (2013.01); *A61F 2002/5056* (2013.01); *A61F 2002/5073* (2013.01); *A61F 2002/6614* (2013.01); *A61F 2002/6621* (2013.01); *A61F 2002/6642* (2013.01); *A61F 2002/6664* (2013.01); *A61F 2002/6692* (2013.01)

(58) Field of Classification Search
CPC .. A61F 2/60; A61F 2/66; A61F 2/6607; A61F 2/76; A61F 2002/5003; A61F 2002/5072; A61F 2002/5073; A61F 2002/5075; A61F 2002/6614; A61F 2002/6621; A61F 2002/6628; A61F 2002/6635; A61F 2002/6642; A61F 2002/665; A61F 2002/6657; A61F 2002/6685; A61F 2002/6692; F16F 1/00; F16F 1/028; F16F 1/04
See application file for complete search history.

(56) References Cited

U.S. PATENT DOCUMENTS

| | | | | | |
|---|---|---|---|---|---|
| 1,151,144 | A | * | 8/1915 | Wofe | A61F 2/66 623/52 |
| 2,470,480 | A | * | 5/1949 | Fogg | A61F 2/66 16/56 |
| 3,754,286 | A | * | 8/1973 | Ryan | A61F 2/66 623/26 |
| 5,685,525 | A | * | 11/1997 | Oguri | B29C 53/083 267/148 |
| 5,913,902 | A | * | 6/1999 | Geible | A61F 2/66 623/52 |
| 6,053,946 | A | * | 4/2000 | Wilkinson | A61F 2/66 623/52 |
| 6,663,672 | B1 | * | 12/2003 | Laghi | A61F 2/66 623/47 |
| 2005/0089363 | A1 | * | 4/2005 | Curtis | A61F 2/76 403/362 |

* cited by examiner

*Primary Examiner* — Thomas J Sweet
*Assistant Examiner* — Christie Bahena
(74) *Attorney, Agent, or Firm* — James L. Sonntag

(57) ABSTRACT

A hollow tubulous composite structure and method for prosthetic limbs is described.

9 Claims, 20 Drawing Sheets

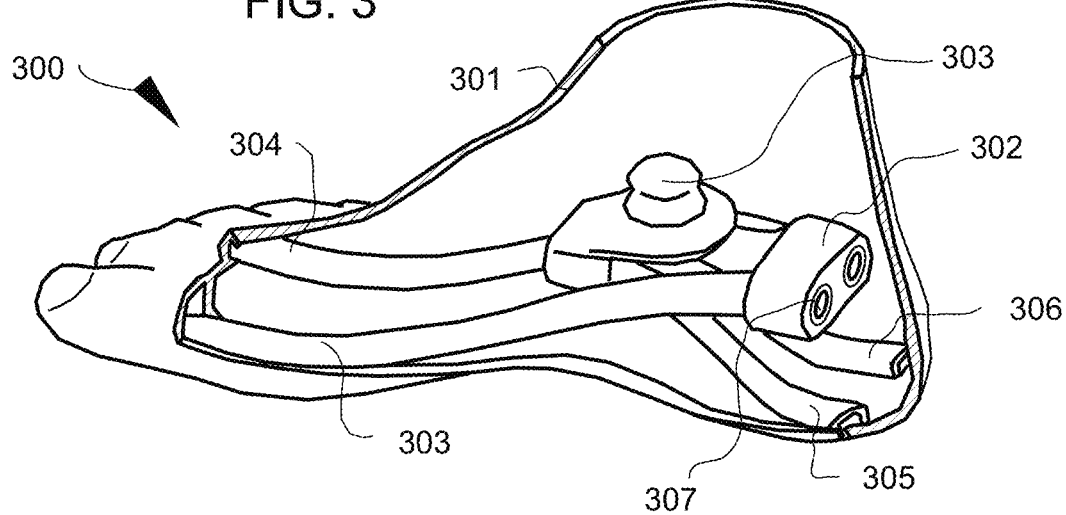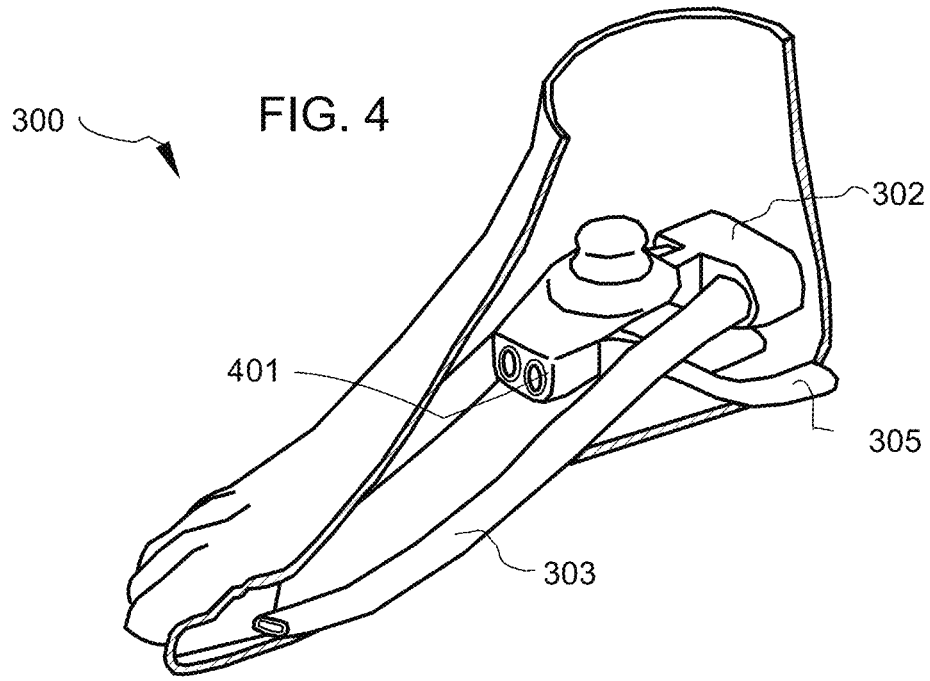

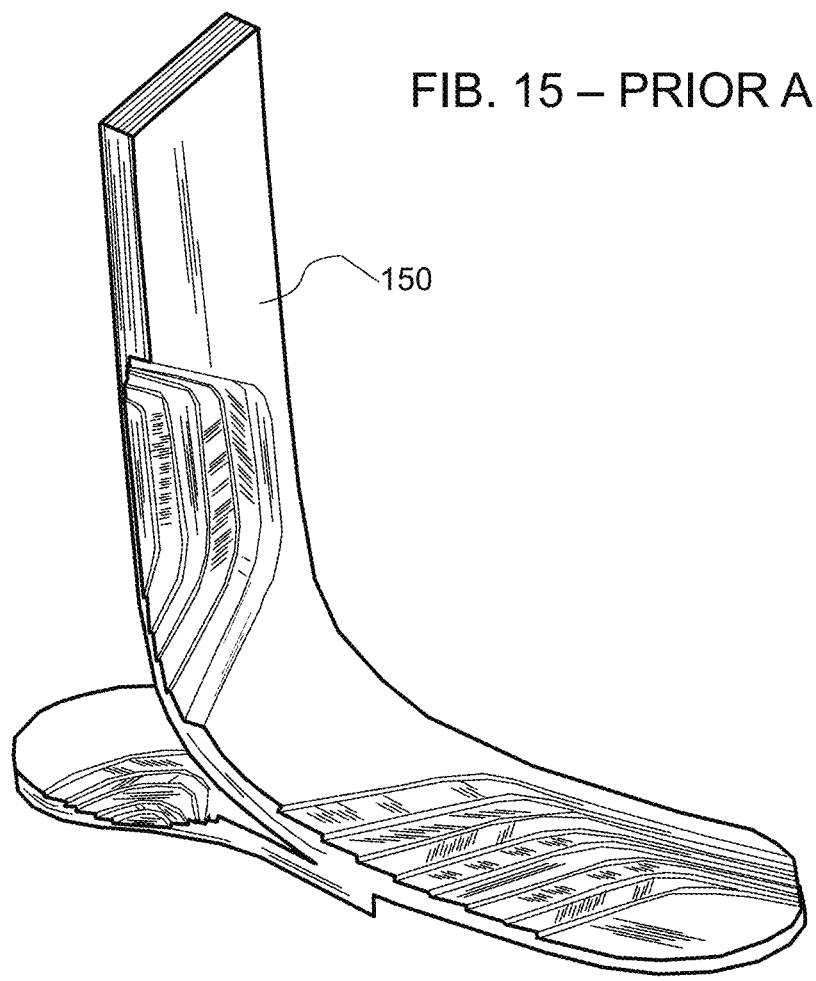
FIB. 15 – PRIOR ART
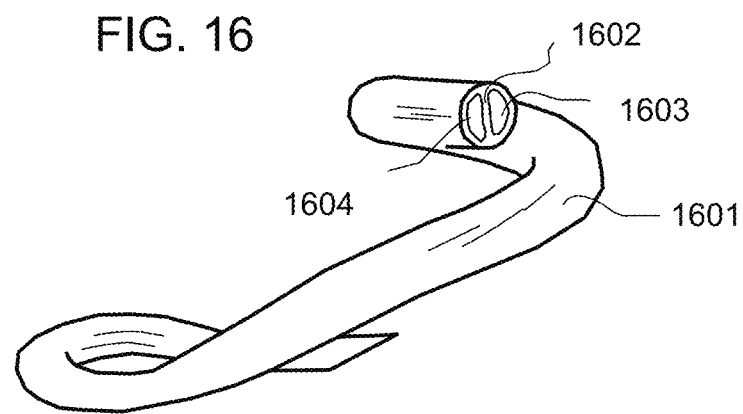
FIG. 16

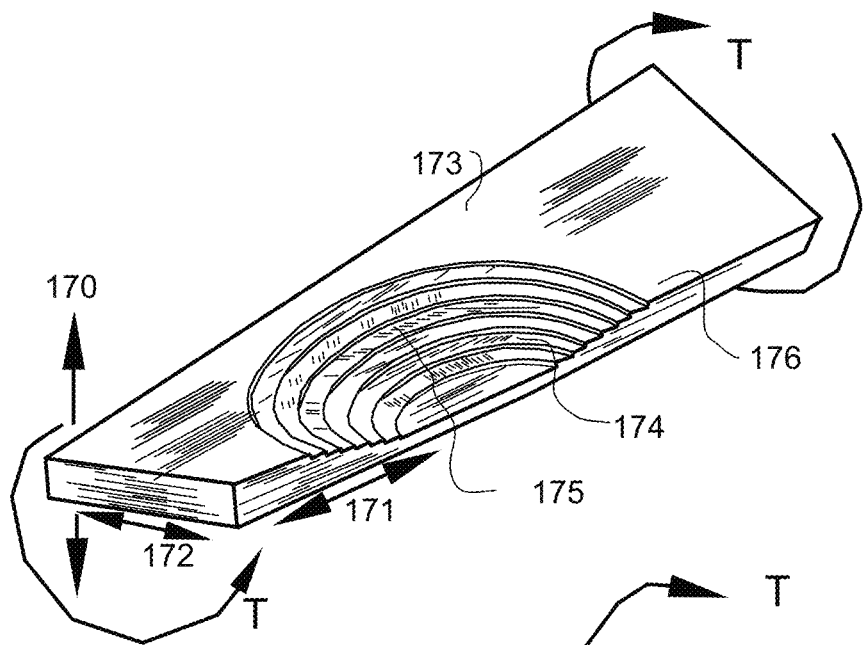
FIG. 17 – PRIOR ART
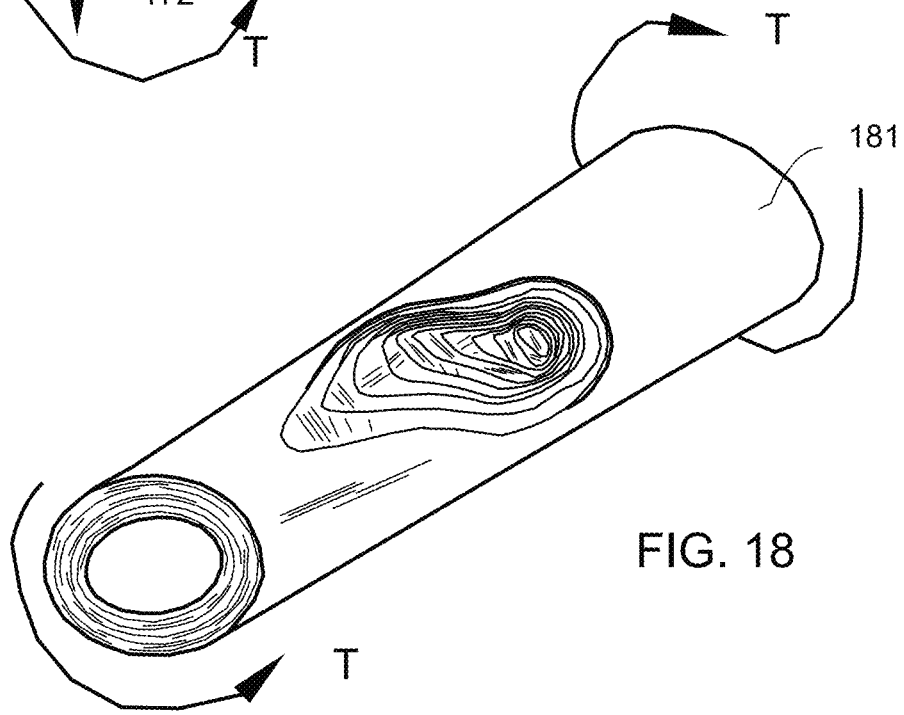
FIG. 18

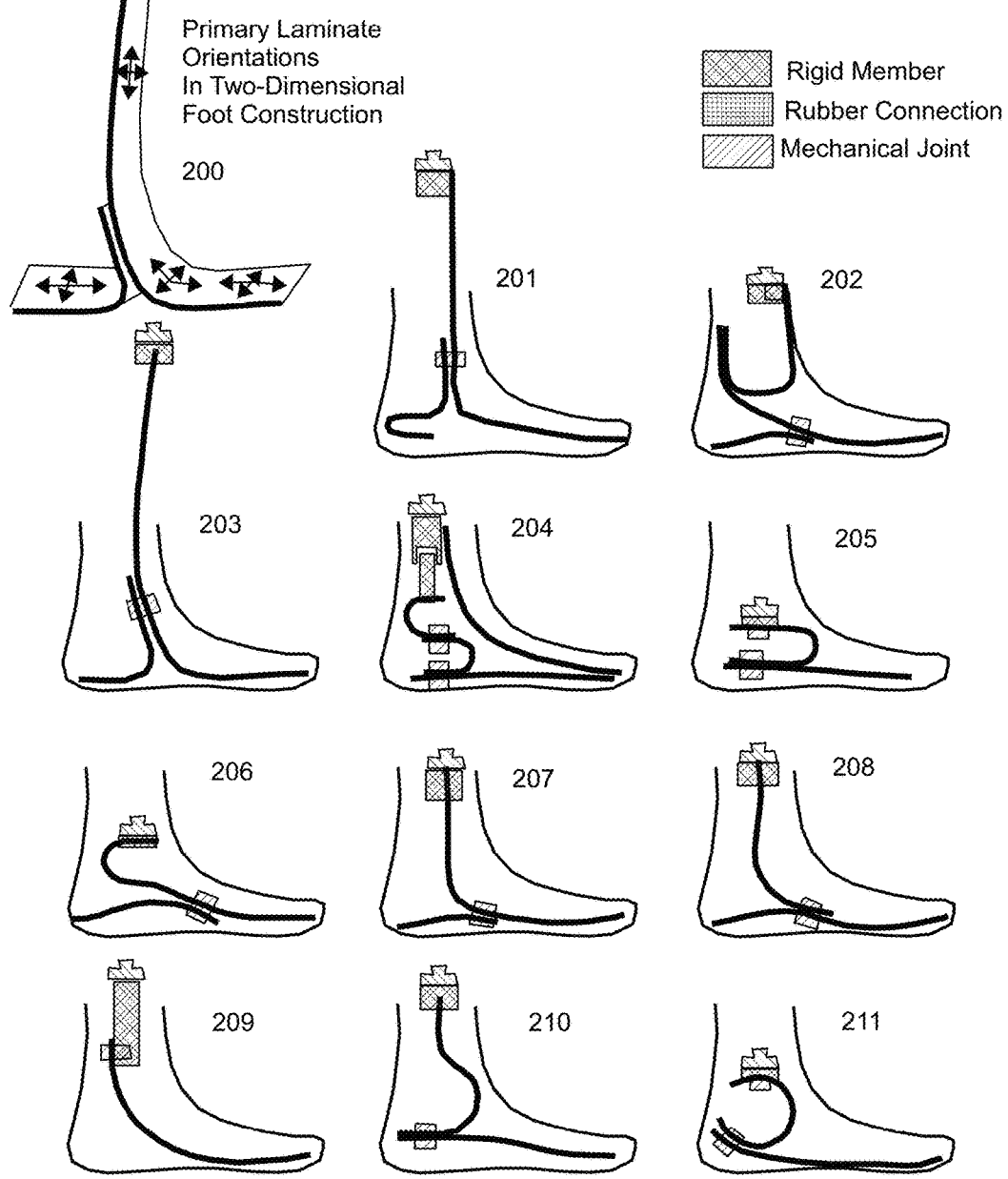

FIG. 26 – PRIOR ART
COMPOSITE LEAF SPRING CONSTRUCTION
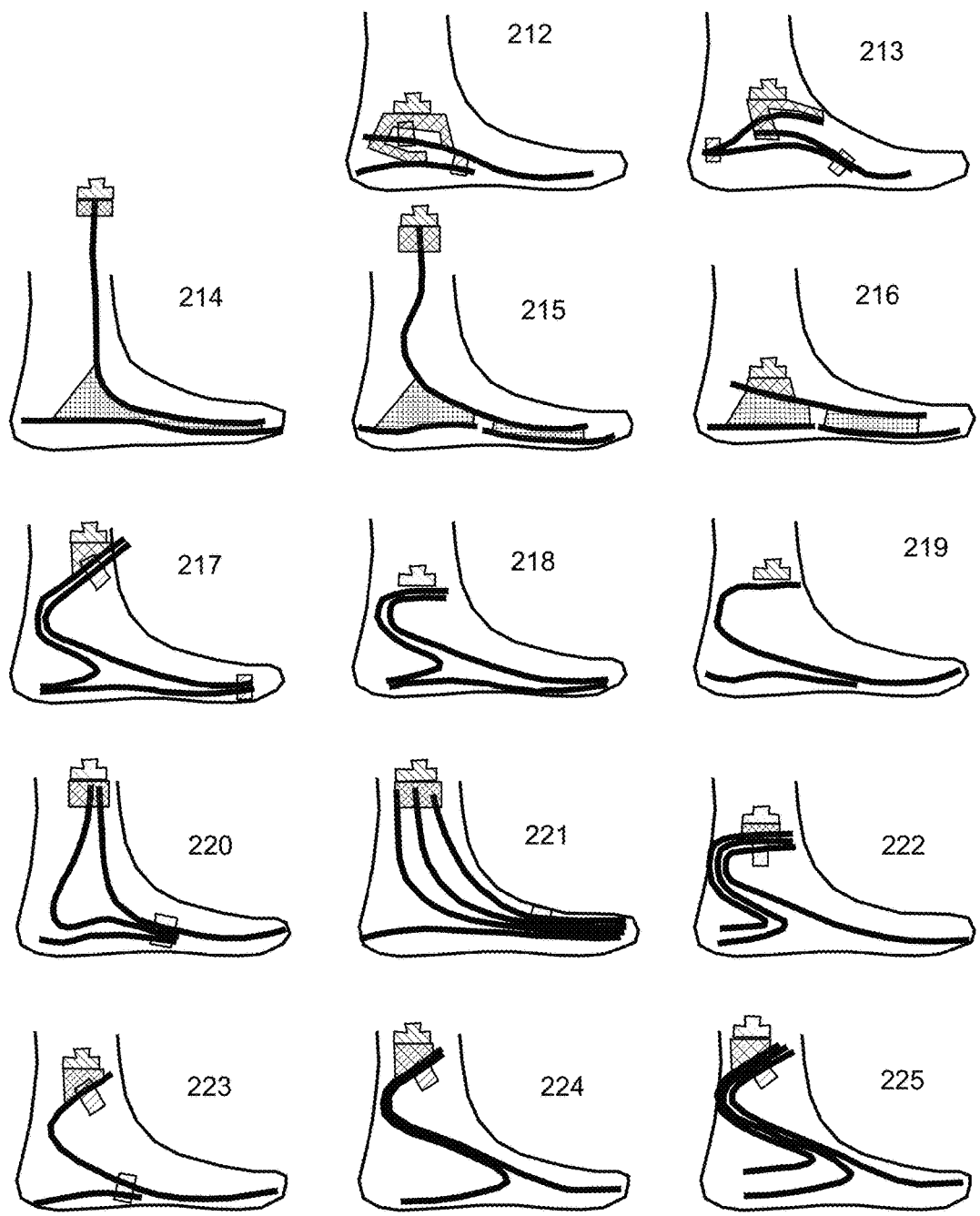

FIG. 27 – PRIOR ART
COMPOSITE LEAF SPRING CONSTRUCTION
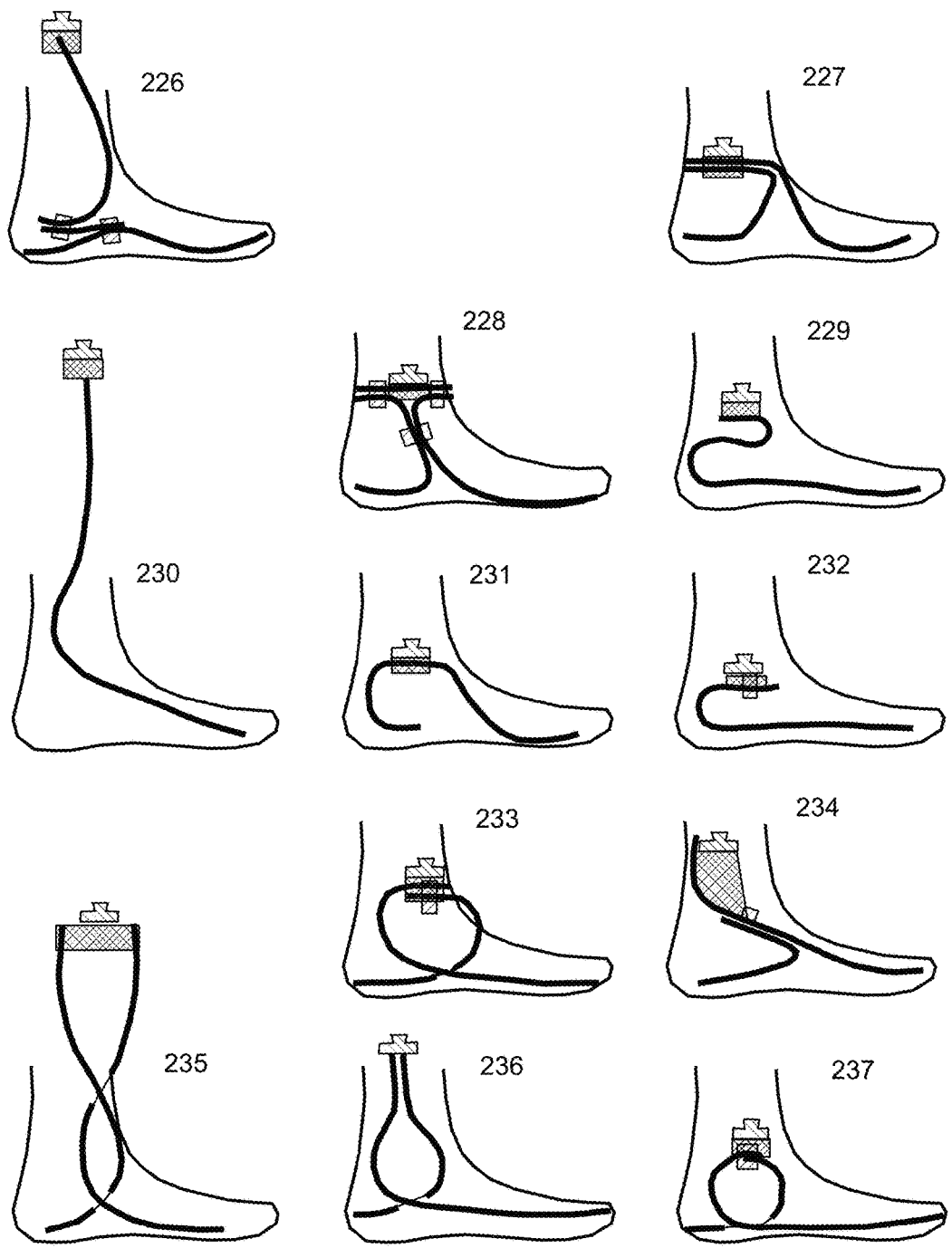

FIG. 28 – PRIOR ART
Composite Leaf Spring Type Construction
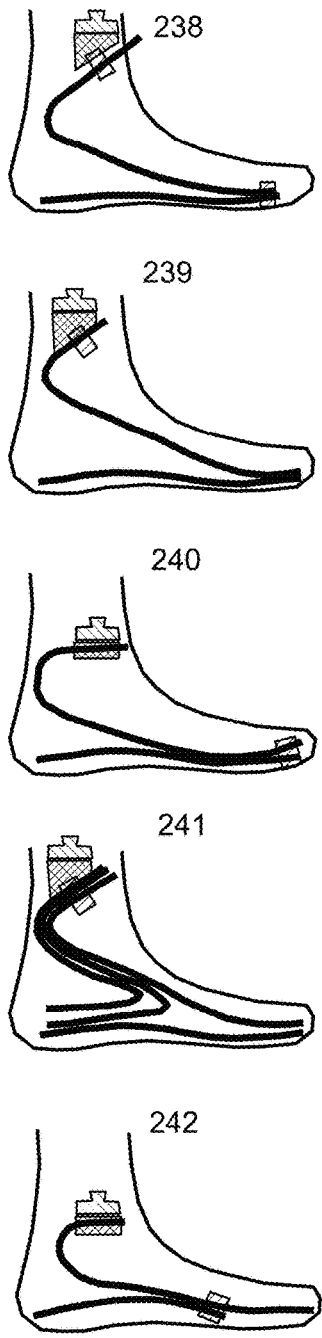
| Prior Art – Composite Leaf Spring Construction | | |
|---|---|---|
| Fig. # | Part # | U. S. Patent Documents |
| 25 | 201 | 4,822,363, 4,547,913 |
| 25 | 202 | 5,549,714 |
| 25 | 203 | 4,822,363 |
| 25 | 204 | 2003/0120354 |
| 25 | 205 | 5,746,773, 2002/0120354 |
| 25 | 206 | 5,514,186, 5,037,444, 6,197,068 |
| 25 | 207 | 6,254,643, 5,549,714, 5,514,185, 4,822,363 |
| 25 | 208 | 5,486,209, 4,822,363 |
| 25 | 209 | 5,514,186, 5,549,714 |
| 25 | 210 | 2002/0087216 |
| 25 | 211 | 6,077,301, 6,099,572, 5,897,594 |
| 26 | 212 | 6,719,807 |
| 26 | 213 | 6,719,807 |
| 26 | 214 | 4,959,073, 6,398,818 |
| 26 | 215 | 2004/0215346, 6,712,860 |
| 26 | 216 | 6,712,860 |
| 26 | 217 | 2004/0068327, 6,929,665 |
| 26 | 218 | 2004/0068327, 6,929,665 |
| 26 | 219 | 6,197,068, 5,037,444, 6,805,717 |
| 26 | 220 | 5,944,760, 6,241,776 |
| 26 | 221 | 6,241,776 |
| 26 | 222 | 2004/0068327, 6,929,665 |
| 26 | 223 | 6,911,052, 6,805,717 |
| 26 | 224 | 2004/0068327 |
| 26 | 225 | 2004/0068327 |
| 27 | 226 | 2004/0186590 |
| 27 | 227 | 5,258,039 |
| 27 | 228 | 5,258,039 |
| 27 | 229 | 6,514,293 |
| 27 | 230 | 5,593,456 |
| 27 | 231 | 5,258,039 |
| 27 | 232 | 5,112,356, 5,941,913, 5,139,525 |
| 27 | 233 | 5,653,767 |
| 27 | 234 | 2004/0068327 |
| 27 | 235 | 5,653,767 |
| 27 | 236 | 5,443,528, 5,571,213, 5,695,527 |
| 27 | 237 | 5,443,528, 5,571,213, 5,695,527 |
| 28 | 238 | 6,911,052 |
| 28 | 239 | Freedom Innovations FS 1000 |
| 28 | 240 | 6,805,717, Freedom Innovations FS300 |
| 28 | 241 | Freedom Innovations Renegade |
| 28 | 242 | Ossur Flex Walk |

FIG. 29 – PRIOR ART
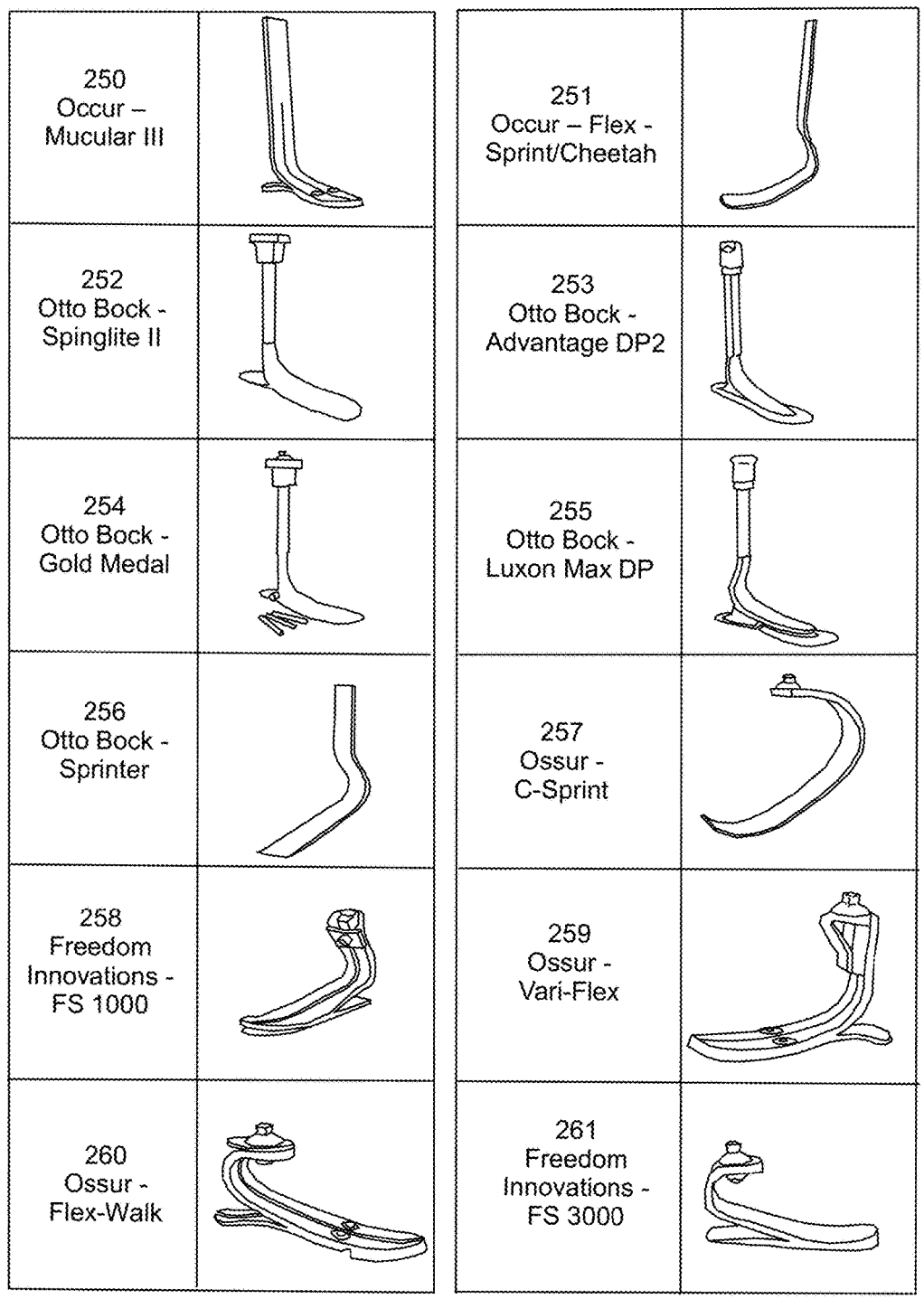

FIG. 30 – PRIOR ART
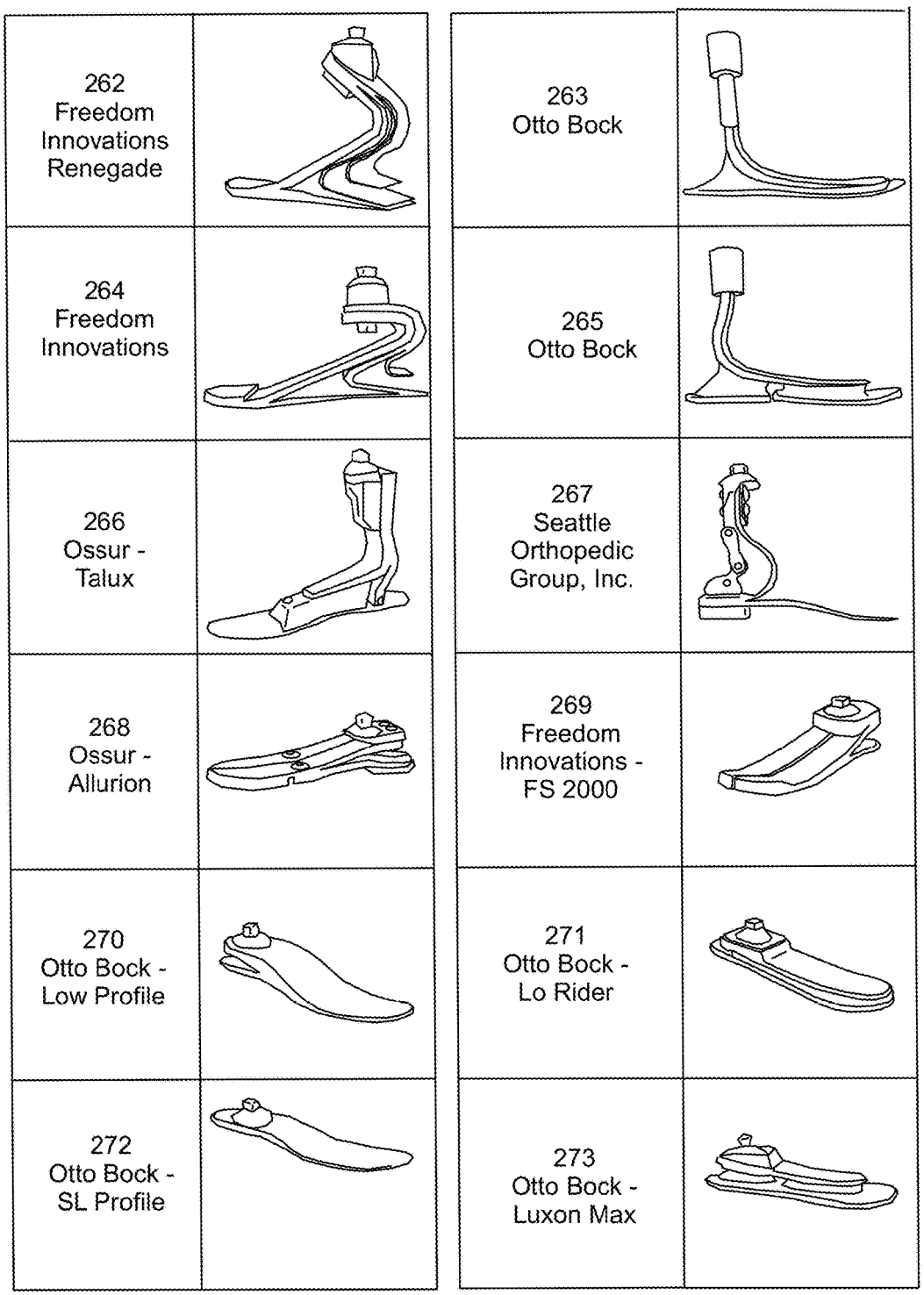

FIG. 31 – PRIOR ART
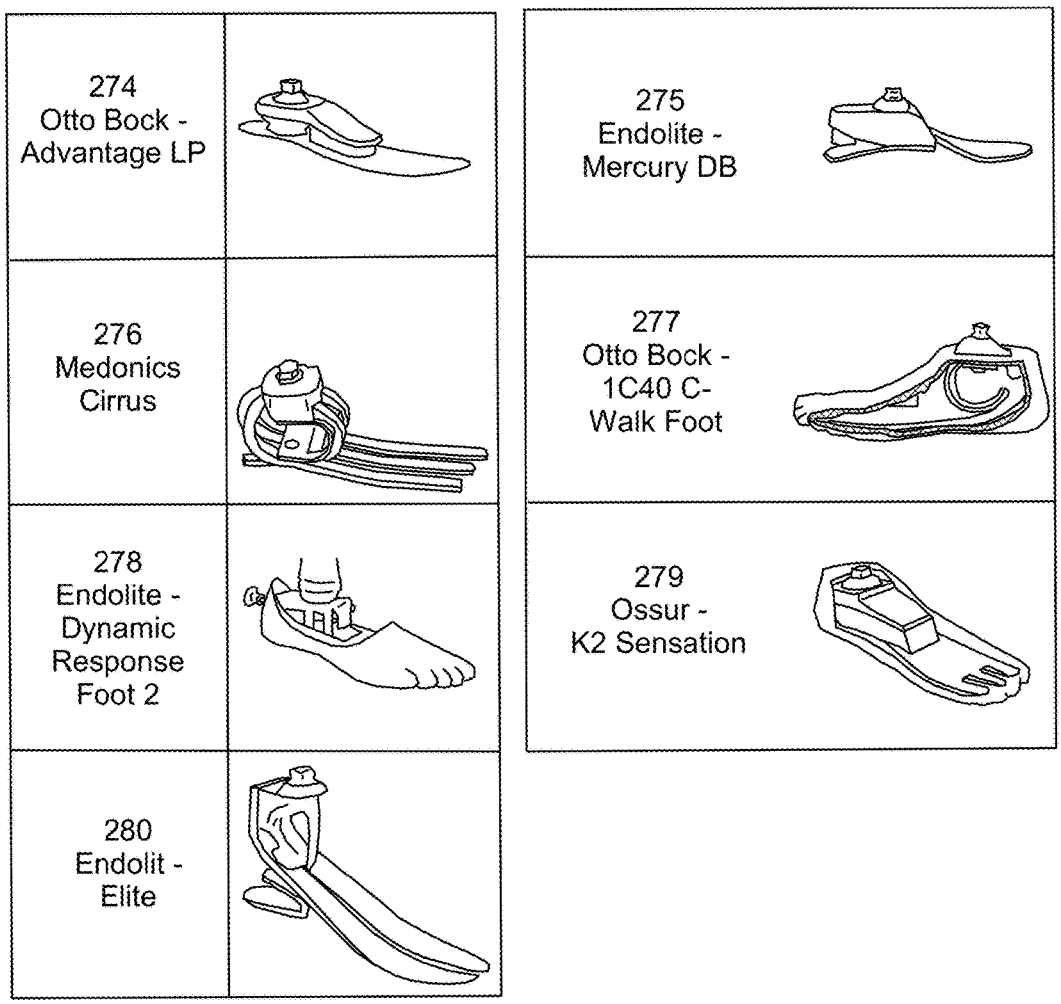

CARBON FIBER PROSTHETIC FOOT WITH HOLLOW CROSS SECTIONS

BACKGROUND OF INVENTION

Function of Prosthetic Feet

Minimizing the weight of the prosthetic limb is very important for the amputee. The comfort and functionality of the prosthetic limb are highly dependent on its weight. This includes reducing the weight of the socket which attaches to the residual limb, and to the various connectors and struts comprising the total prosthetic limb. The most important areas where weight should be reduced are those on the distal portion of the prosthetic limb, i.e. the foot itself.

It is also very important that prosthetic feet do not fail in service to prevent injury and inconvenience to the amputee. Also, the prosthetist, who has a strong influence on a patient's foot choice, incurs cost to replace the failed foot. Prosthetic feet utilizing mechanical elements, i.e. pivot joints etc., have a markedly higher rate of in service failure than feet without such complicating design features. This has been an additional advantage of the carbon fiber prosthetic feet currently available.

Nature of Composite Materials

Composite materials, such as carbon-fiber/epoxy, provide a higher material stiffness and strength for a given weight than traditional materials. Consequently, these materials have found wide use in prosthetic feet.

High performance composite materials combine two or more materials with different mechanical characteristics. Taken separately, these constituent materials may not have the necessary properties for high strength structural applications. However, in combination, the resultant composite material can be a high performance structural material.

Carbon-fiber/epoxy illustrates this phenomenon. Epoxy resin is a relatively weak material with a relatively low stiffness. It has a tensile strength of roughly 10 Ksi. and a tensile modulus of roughly 750 Ksi. Its stress strain behavior is also nonlinear, showing a marked decrease in shear and tensile stiffness at higher elongations. For comparison, high strength steel has a tensile strength of approximately 100 Ksi. and a modulus of 30 Msi.

In contrast, carbon fiber has a very high tensile strength and stiffness in the fiber direction. It typically has a tensile strength of roughly 700 Ksi. and a very linear tensile modulus of roughly 33 Msi. That makes the fiber about 70 times stronger, and 50 times stiffer than the epoxy matrix material. However, the carbon fiber alone is not particularly useful as a structural material. It consists of a multitude of essentially continuous, very small fibers with virtually no compression strength, no shear strength, nor any mechanical properties transverse to the fibers.

Carbon-fiber/epoxy combines the best aspects of the constituent materials. The epoxy resin serves to transfer shear between fibers, stabilizes the fibers to support compressive loads, and provide some strength in the direction perpendicular to the fibers. An exemplary resultant material in its unidirectional form has a modulus of about 21 Msi. and strength of about 300 Ksi. in the fiber direction, and a density roughly one fifth that of steel. Composites allow the manufacture of prosthetic feet which are much lighter weight, and have higher energy storage capacities than what can be obtained using traditional metal structures alone.

Limitations of Composite Materials in Transverse Direction

Just as the advantages of fiber reinforced plastic materials are utilized when designing new prosthetic feet, the material's limitations must also be taken into consideration. These are material limitations that would not impact the design of traditional metal structures for example Composite materials' primary limitation is its lack of material strength in directions that fibers are not oriented with. For example, for carbon-fiber/epoxy, in spite of the very high strengths in the fiber direction, its strength transverse to the fibers is only about 10 Ksi., basically the same as the unreinforced epoxy. A secondary limitation relates to the relative difficulty of fabricating complex shapes. Reference is now made to FIG. 17. which is a schematic of a laminate with partially cut away 174 to illustrate the different plies of the laminate. Arrows 171 and 172 indicate the in-plane directions. Arrow 170 indicates the out-of-plane direction. The present invention was developed to address both of these problems, which to date have not been addressed by composite prosthetic feet.

The reinforcing fibers provide the vast majority of load carrying capability in the composite. Consequently, composite structures are relatively weak and flexible when loaded in directions without fibers oriented in those directions. High performance composite structures need to have fibers aligned in every highly loaded direction to produce a structure with optimal efficiency.

Planar Nature of Composite Materials

Another characteristic of high performance composite structures is that they are usually planar in nature. One reason for this is the form of the raw material.

Perhaps the most common form of the raw material is unidirectional "prepreg". In this form, a semisolid epoxy resin is preimpregnated into a thin sheet of fibers all aligned in a single direction. A cut away view of a typical laminate 173 is shown FIG. 17. The individual plies arranged in different orientations are denoted by 174, 175, and 176. Using this type of resin, a partially cured tacky semisolid material at room temperature, produces a sheet of handlable coherent material.

Another very common form of the raw material can be produced by first weaving fiber bundles into a flat cloth prior to being preimpregnated. Therefore the most common forms of the raw material are supplied as essentially very thin planar materials. These sheets or layers of material are laid upon each other at distinct orientations depending on the anticipated loads in those directions. These directions are restricted to being in the plane of the laminate, 171 and 172 in FIG. 17. This "layup" then forms a laminate with relatively high structural performance in-the-plane of the laminate. This belies the importance of the terms, "in-plane" 171, 172 or "out-of-plane" 170, commonly used in the composites industry.

The simplest composite structures to fabricate are flat or curved in only one direction. It is much simpler to assemble the planar raw material in shapes with curvature in only one direction, or with only a slight curvature in the opposite direction.

It is far more difficult to manufacture composite laminates/components having complex geometric shapes. That includes laminates which have a high degree of curvature in two orthogonal directions, i.e. compound curvature. Complex shaped composites structures are therefore less common than structures with laminates curved in primarily in one direction.

However, the structures containing laminates with a high degree of compound curvatures, i.e. more complex geometric shapes, have the potential to be far stronger and more efficient than the simpler geometries. These structures can be designed to allow the fibers to be aligned in all the load directions, rather than relying on the relatively week epoxy resin to carry the load.

Current Leaf Spring Type Prosthetic Feet

Referring now to FIGS. 15, 19, 20, and 25-31; in the past, dynamic response feet have primarily used a Composite Leaf Spring construction to store and release energy during gait. Some of the most widely recognized commercial embodiments of dynamic response feet, shown in FIG. 29-31, include Flexfoot by Ossur, Springlite by Otto Bock, Seattle feet by Seattle Systems and Carbon Copy by Ohio Willow Wood. All of these feet have been successful commercially and widely distributed.

These leaf spring type prosthetic foot designs are archetypical of the current state of the art of technological development in prosthetic feet. The foot 150 shown in FIG. 15 illustrates the most common features of these type of feet. FIGS. 25-28 illustrate the wide range of prior art prosthetic foot designs using this design approach. As seen in FIGS. 29-31, many of these designs have been reduced to commercial products. They rely primarily on bending or flexural stresses to store energy. Nearly all these have an initial curvature in only the fore-aft directions, being essentially straight in the lateral direction. Energy is stored and released primarily through flexure of the leaf spring like components and the design is two dimensional in nature.

In general, these Composite Leaf Spring foot designs require that transverse shear loads in the foot be carried by the epoxy matrix in "out-of-plane" shear. In fact the transverse shear strength of the laminate will commonly be the limiting strength factor affecting the foot design. For this reason, manufacturers of the current leaf spring type feet will typically select a prepreg carbon fiber material with the highest transverse shear strength available (measured as short beam shear strength).

Typical Structural Stresses and Strains in Prosthetic Feet

In general there are four critical types of internal loads in composite prosthetic foot structures, including: bending loads, transverse shear loads, interlaminar tensile loads, and torsional loads.

Bending loads are quite common in many structures. They are easy to understand, because it is possible to have a structure in pure bending, having no other internal loading. Bending loads produce bending stresses in the structure. These are axial stresses that vary across a cross section of the structure.

In contrast transverse shear loads are more difficult to conceptualize. Internal transverse shear load always give to internal bending loads. The two types of internal loading are interdependent. The form of this relationship in a simple structure is defined by the engineering equation $V=dM/dx$, where M is the moment and V is transverse shear. Specifically, the transverse shear in a structural member is equal to the rate of change of the moment down the length of the member. Almost all structural loadings in the real world include transverse shear. Transverse loads produce shear stresses, in addition to creating internal bending moments.

The design limitations inherent in Composite Leaf Spring feet make them very susceptible to interlaminar tensile stresses which can easily exceed the strength of the relatively weak epoxy matrix material. These stresses would typically produce delaminations in curved laminate areas. These stresses are produced when an initially curved section in the foot is loaded so as to open or flatten or flatten the curve. Arrow 191 in FIG. 19 indicates the location of these tensile stresses during the heel strike portion of the gait which can cause delamination. Arrow 201 in FIG. 20 illustrates how this tensile stress switches to a compressive stress during the toe off portion of the gait cycle. This type of delamination failure in laminated composites does not occur in metal structures.

Torsion is twisting force, a bending force actually, but applied transverse to the primary axis of the structure. Torsional loading, denoted as T, produces a shear stress. A torsional shear stress is a shear stress that varies across the cross section of the structure in a fashion similar to the way a bending axial stress varies across a cross section. The tubulous composite member 181 shown in FIG. 18 illustrates how prosthetic feet of the present invention can efficiently store energy in torsional stresses through in-plane loading, as opposed to the flat laminate member 173 shown in FIG. 17 illustrating that current Leaf Spring type prosthetic feet which cannot store significant energies as torsional stresses because they produce out-of-plane stresses.

Structural Mechanics of Spring Design

The energy storage or dynamic response prosthetic feet owe a large part of their performance to their ability to store energy during one portion of the gait and release it during a subsequent portion of the gait cycle. In essence these prosthetic feet act like springs. The weight of these springs is dependent on the structural efficiency of their design and materials used.

The structural efficiency and mechanical characteristics of springs is a well understood part of engineering mechanics. In particular there are several rules of thumb that experienced spring design engineers know intuitively. One of these rules is that stressing the spring material more evenly or uniformly increases efficiency, i.e. remove the material which is stressed less and is therefore less efficient. Increasing the wire length (length of active spring material) of a spring can be used to reduce stresses, increase maximum deflection, increase energy storage capacity. Obtaining a more compliant spring without failing requires a longer wire length. The only way to get a longer wire length into the constrained space envelope of a prosthetic foot is to coil it.

Traditional Autoclave Manufacturing Technology

An autoclave manufacturing process is utilized on most current composite construction dynamic response prosthetic feet. This process uses a single sided tool to produce components which are generally planar in nature. The shapes are usually curved in only one primary direction. The autoclave process is expensive and slow and is unsuited for the manufacture of hollow shapes with a complex geometry.

The material near the mid-plane of this planar structure are relatively inefficient, contributing weight but not capable of storing significant flexural energy. Most dynamic response prosthetic feet today are of relatively simple construction, being essentially planar in direction. Such feet are generally store energy almost exclusively in flexure. Delamination failures occasionally occur in current dynamic response prosthetic foot designs when the structure is loaded in a way to incur interlaminar tensile stresses or when interlaminar shear stresses exceed the strength of the relatively weak matrix material, usually epoxy resin, such as when a curved section in the foot is loaded so as to open or flatten or flatten the curve.

Delamination occurs because there are no fibers oriented in the direction of the tensile or shear load. Current autoclave construction processes are not conducive to the construction of structures which can place fibers in the direction where these tensile or shear delamination type loads are transmitted.

SUMMARY OF INVENTION

Tubulous Composite Prosthetic Feet

The present invention relates to prosthetic feet and specifically to prosthetic feet containing composite structural elements that are tubulous or tubular in nature. These tubulous composite structural elements generally contain closed-cross-sections formed around longitudinally hollow or elongated hollow cavities. The length of these tubulous elements, as measured along its primary longitudinal path, is much longer than its mean diameter. These tubulous elements might also be described as having a geometry or other properties similar to a hose, pipe, duct, conduit, channel, or artery.

In order to provide a dynamic response foot prostheses, the present invention comprises a mounting element such as an ankle plate adapted for attachment to a lower leg pylon and a tubulous composite structural element or elements which serve to store and release energy at different points of the gait cycle. The tubing or tubulous shape may, for example, form a helical spring whose major axis could be oriented in positions.

Hollow Molding Technology

The tubulous composite structural elements of the present invention are more difficult to fabricate, more sophisticated, and more highly engineered then typical autoclave cured leaf spring type feet. The structural elements are tubulous in nature containing closed-cross-sections formed around elongated hollow cavities. It is a more refined and modern product, made with a more advanced and modern manufacturing process.

The preferred manufacturing technology to create the shaped hollow composite tubes utilizes matched female molds with an internal cavity forming the outer shape of the product. A typical process might involve placing a resin impregnated fiber material in the tubular cavity or wrapped about an internal pressure bladder which is placed into the cavity. Several examples of this manufacturing technology are disclosed as used in various industries in present U.S. Pat. Nos. 5,624,519; 6,340,509; 6,270,104; 6,143,236; 6,361,840; 5,692,970; 5,985,197; 6,248,024; 5,505,492; 5,534,203; and 6,319,346. The advanced product designs and manufacturing processes described in these patents is now commonly used in a few product areas, including bicycles and bicycle components, and sports racquets and poles of various types. However, these advanced processes have not been previously used in the prosthetic foot industry.

There are several reasons why the manufacturing process is more difficult and more highly engineered. In autoclave manufacture the exact width and length of material placed on a mold prior to cure are not particularly critical. In contrast, the comparative dimension called the width of the material in the complex shaped tubulous structures of the present invention is quite critical because it has to be sized to exactly fill and mate with the entire outer mold line surface, the internal cavity, of the mold. The methods of forming the preforms placed into the molds are also far more difficult. The forming process must not compress the laminate in the plane which tends to form waves.

Advantages of the Invention

Accordingly, by practice of the invention an improved prosthetic foot of hollow composite tubing can be produced at reasonable cost. The prosthetic foot has high strength, great reliability, high level of compliance and terrain conformance. In addition, a prosthetic foot of hollow composite tubing can be produced in a fashion that allows a wide range of geometries to be utilized effectively in foot structure, while providing a relatively light-weight foot capable of supporting and storing high torsional and radial tensile loads with fibers oriented in a way to avoid large interlaminar tensile or shear stresses.

BRIEF DESCRIPTION OF DRAWINGS

FIG. 3 illustrates a foot design with four separate lightly curved tubulous limbs inside a cutaway view of a cosmesis.

FIG. 4 illustrates another view of the four limbed foot.

FIG. 10 illustrates a molding tool for the

FIG. 12 illustrates a molding tool for the

FIG. 15 is a schematic illustrating a prior-art prosthetic foot construction.

FIG. 16 illustrates a double lumen variant of the tubulous coil member of FIG. 1.

FIG. 17 is a schematic illustrating the solid flat laminate typical of a prior-art prosthetic foot construction.

FIG. 18 is a schematic of tubulous composite member typical of the present invention.

FIG. 25 shows schematics illustrating prior-art prosthetic foot constructions.

FIG. 26 shows schematics illustrating prior-art prosthetic foot constructions.

FIG. 27 shows schematics illustrating prior-art prosthetic foot constructions.

FIG. 28 shows schematics illustrating prior-art prosthetic foot constructions.

FIG. 29 shows schematics of commercial products illustrating prior-art prosthetic foot constructions.

FIG. 30 shows schematics of commercial products illustrating prior-art prosthetic foot constructions.

FIG. 31 shows schematics of commercial products illustrating prior-art prosthetic foot constructions.

DETAILED DESCRIPTION

An embodiment is a prosthetic foot comprising a mounting element and a tubulous fiber composite member. The mounting element is securable to a lower limb prosthetic structure. The tubulous fiber composite member is attached to the mounting element, and is in the form an elongated hollow shape or shapes that follow a not-straight path corresponding to a longitudinal centerline of the shape.

Figure 21:
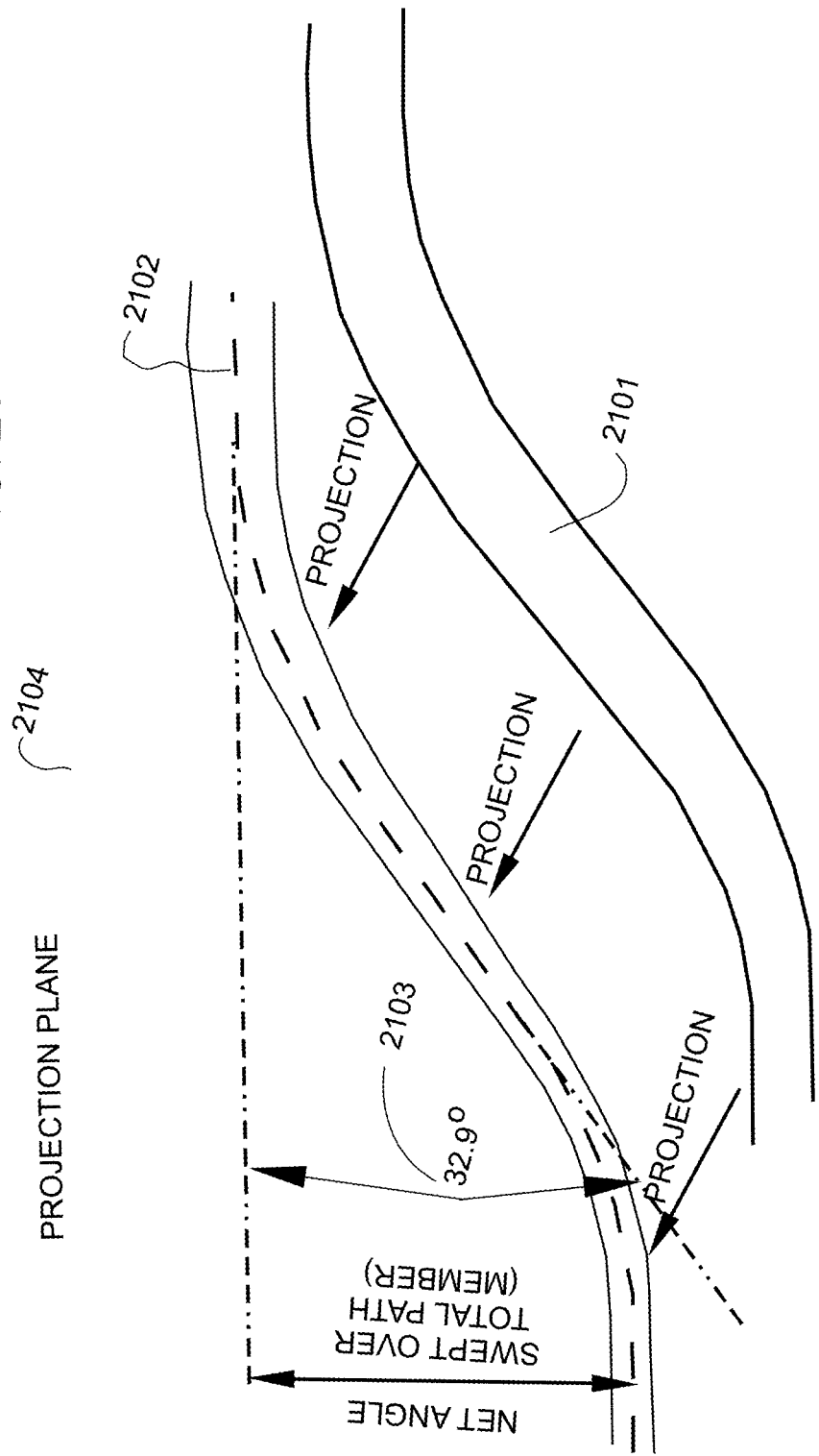
FIG. 21 illustrates the method for projecting the longitudinal centerline path of a tubulous member onto a plane for calculating the angular sweep.

The path sweeps an angular change between two points located on the path. The angular change is measured by projecting the path onto a plane fixed in space with respect to the foot. Referring to FIG. 21, shown is an exemplary tubulous fiber composite member 2101, the path or longitudinal center line 2102, and a projection plane 2104 upon which the path is projected. The incremental angle swept 2103 by the path 2102 in this case between points A and B is 32 degrees. This is just the incremental angle swept over a portion of the path, not the total angle swept over the entire length of the particular tubulous member. The path can be projected upon any of the three primary planes defined by any two the three primary axes shown in FIG. 1, i.e. the vertical, lateral, or fore-aft axes.

In addition, where there are two or more hollow shapes, or there is branching from one to two or more paths, the angular change can be measured between any two points on the structure.

Figure 1:
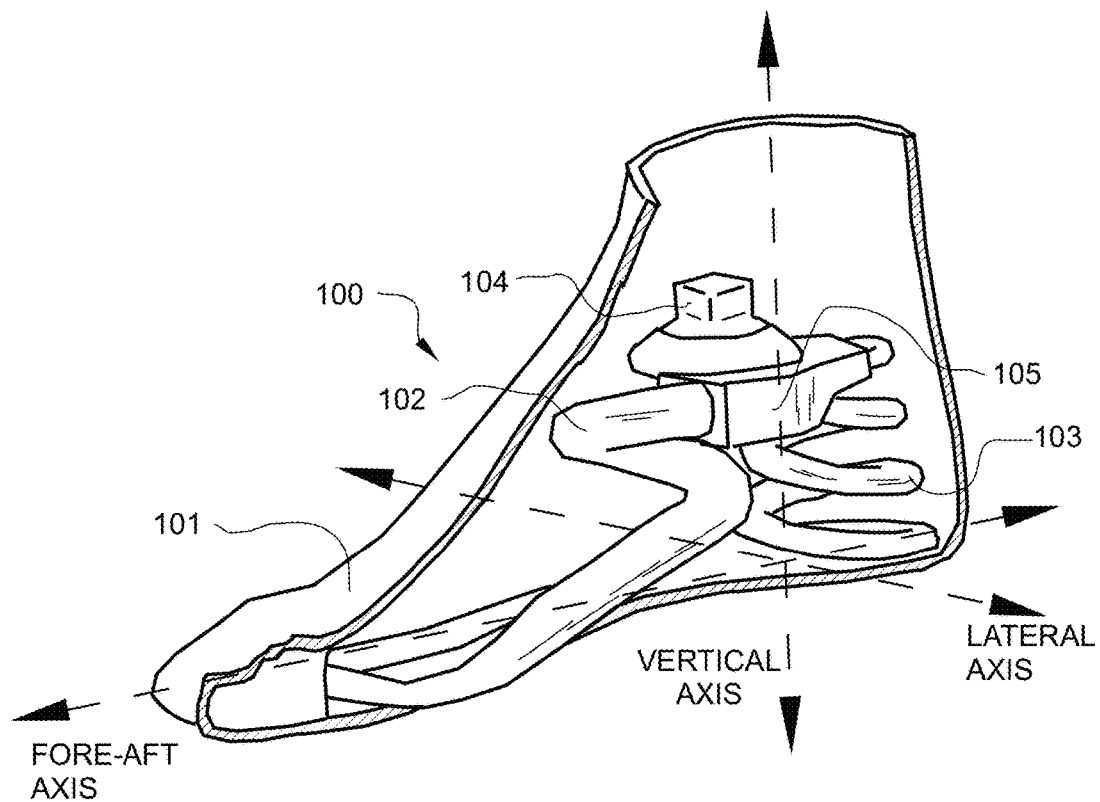
FIG. 1 illustrates a double coil design inside a cutaway view of a cosmesis.

Reference is now made to FIG. 1. For the purposes of this description, the three principle axes of a prosthetic foot are referred to as the fore-aft axis running forward and backward through the middle of the foot in a horizontal orientation; the lateral axis oriented side-to-side, 90 degrees to the fore-aft axis of the foot; the vertical axis oriented vertically.

The fiber composite shape is formed by fiber plies with fibers in each ply oriented in a particular direction. For sustaining loads that are subjected to the foot, there are plies oriented at +45 degrees, −45 degrees, and 0 degrees with respect to the direction of the path or longitudinal centerline. These degree values are nominal values, and actual orientations within plus or minus 20 degrees is acceptable for most shapes.

Figure 7:
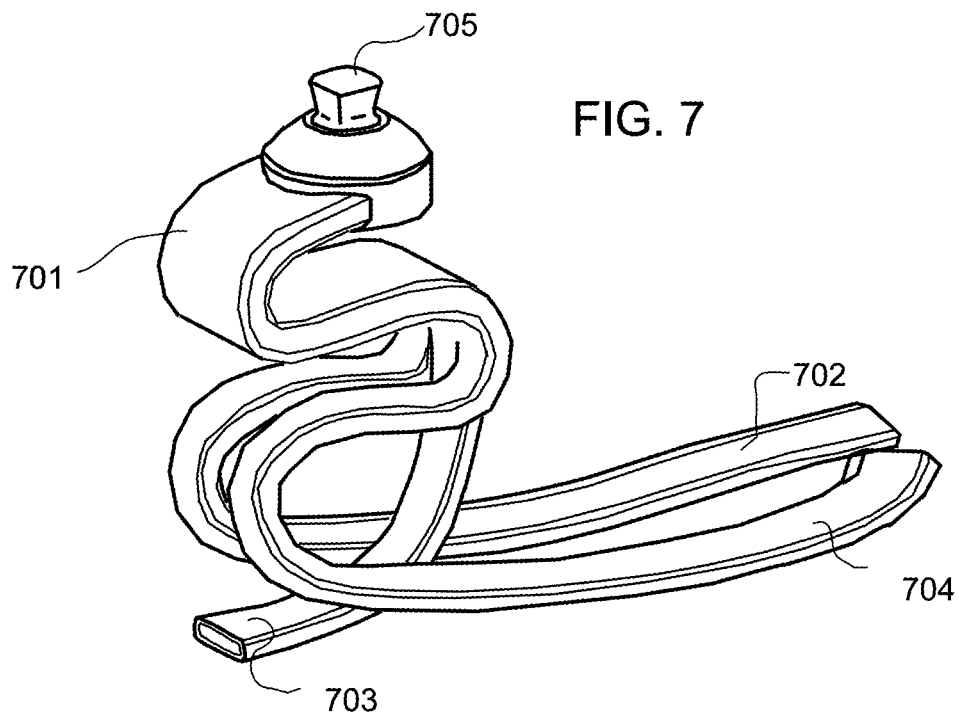
FIG. 7 illustrates sulcated tubulous member.
Figure 8:
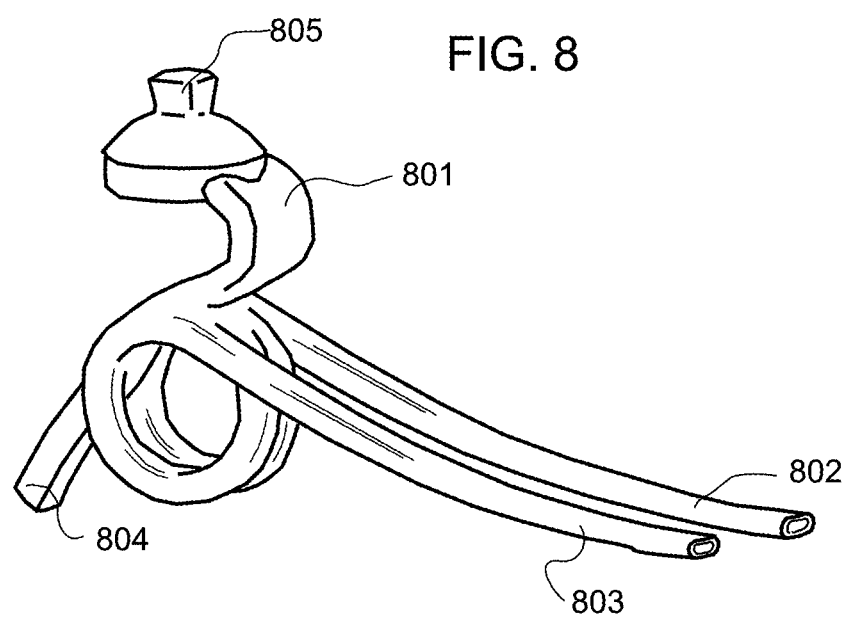
FIG. 8 illustrates sulcated tubulous member.

The tubulous fiber composite member can comprise one hollow shape or more than one hollow shape, i.e., there can be one or more separate paths. For example, composite member can comprise a shape or shapes over the heel 305, 306, and separate shape or shapes 303, 304, directed toward the toe of the foot (See FIGS. 3 and 4). One composite member 605 may optionally branch into "toes" 602, 603 (See FIG. 6). In addition, a member with a path 701 can diverge from one to two or more members and paths 702, 703, 704, and multiple paths can converge to fewer or one path. (See FIGS. 7 and 8). For each hollow shape, the hollow may be continuous or subdivided into multiple hollows. For example, in FIG. 16 is shown a shape with an internal wall 1602 extending generally along its path that subdivides the hollow into two hollow chambers 1603 and 1604, or lumens.

Figure 2:
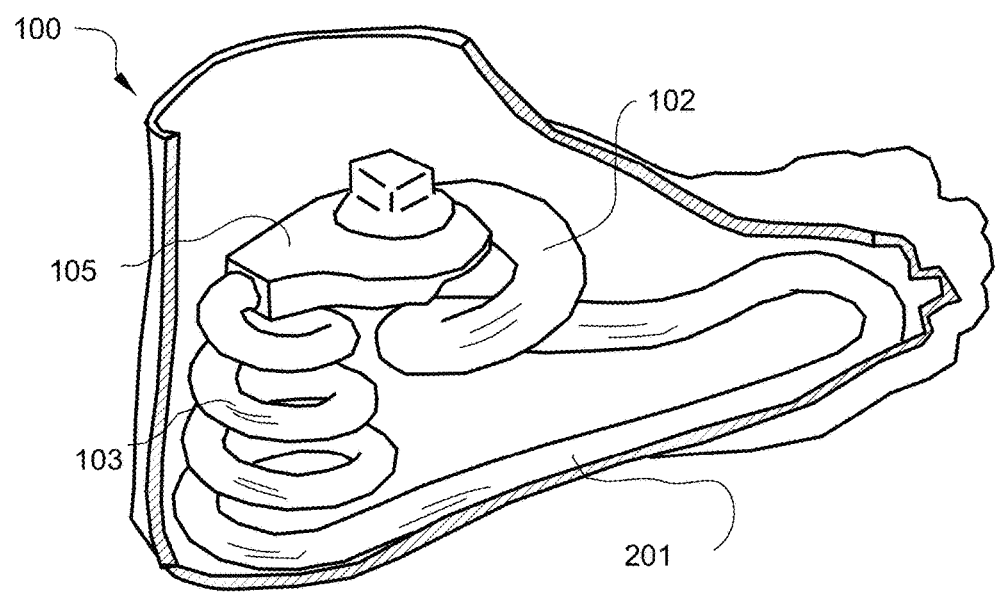
FIG. 2 illustrates another view of the double coil design.
Figure 5:
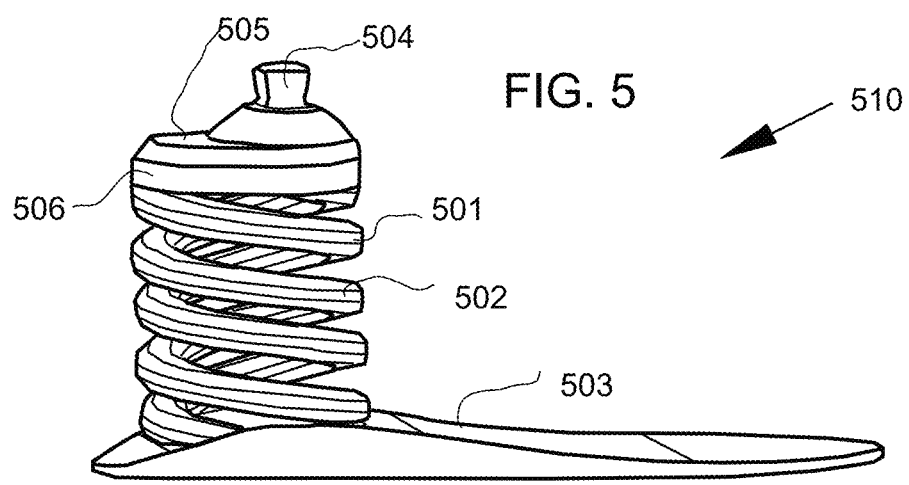
FIG. 5 illustrates a nested double coil foot design.

The composite member can have any suitable cross-section, such as, for example, circular, ovoid, polygonal, rectangular, and the cross-section can vary along the longitudinal center line both in size and shape. Examples of composite members are shown in the figures. FIG. 5 part 501 shows a composite member having a hollow shape configured as a helix with an axis parallel the vertical axis. FIG. 2 part 103 shows a composite member having a hollow shape configured as a tapered helix with an axis parallel the vertical axis.

Figure 10:
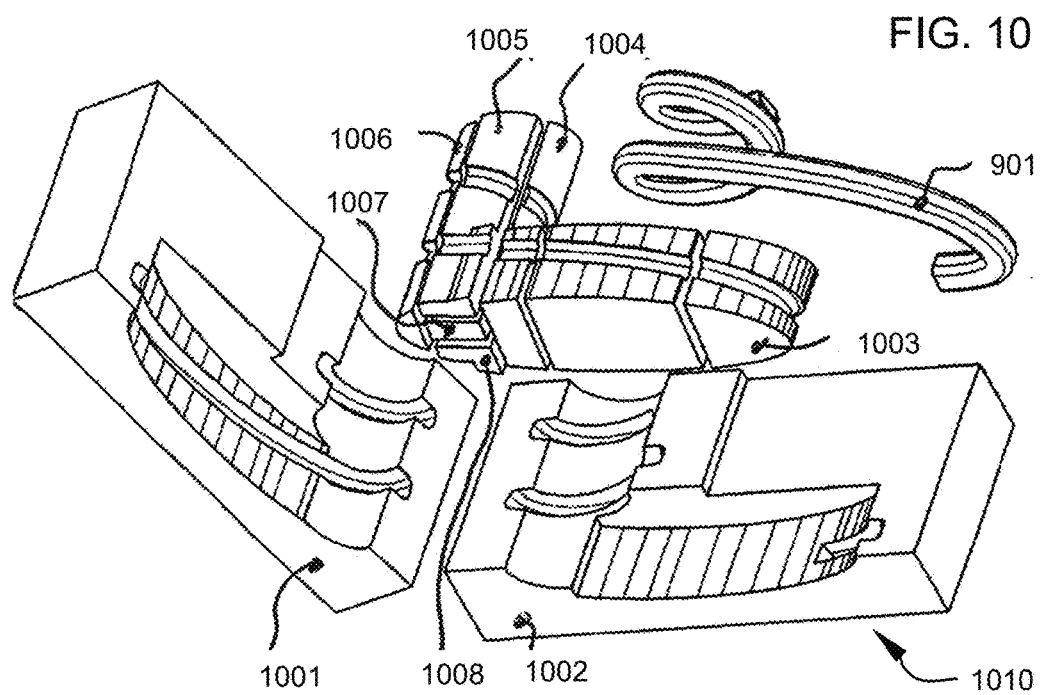
Figure 12:
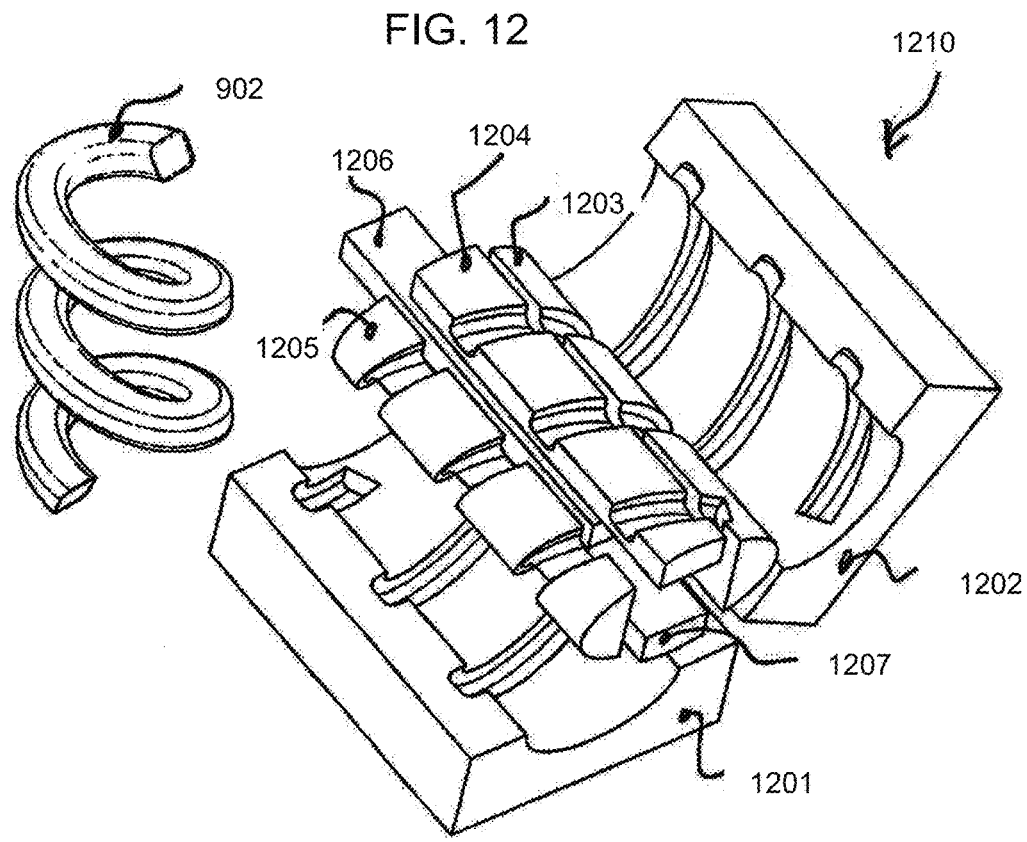
Figure 13:
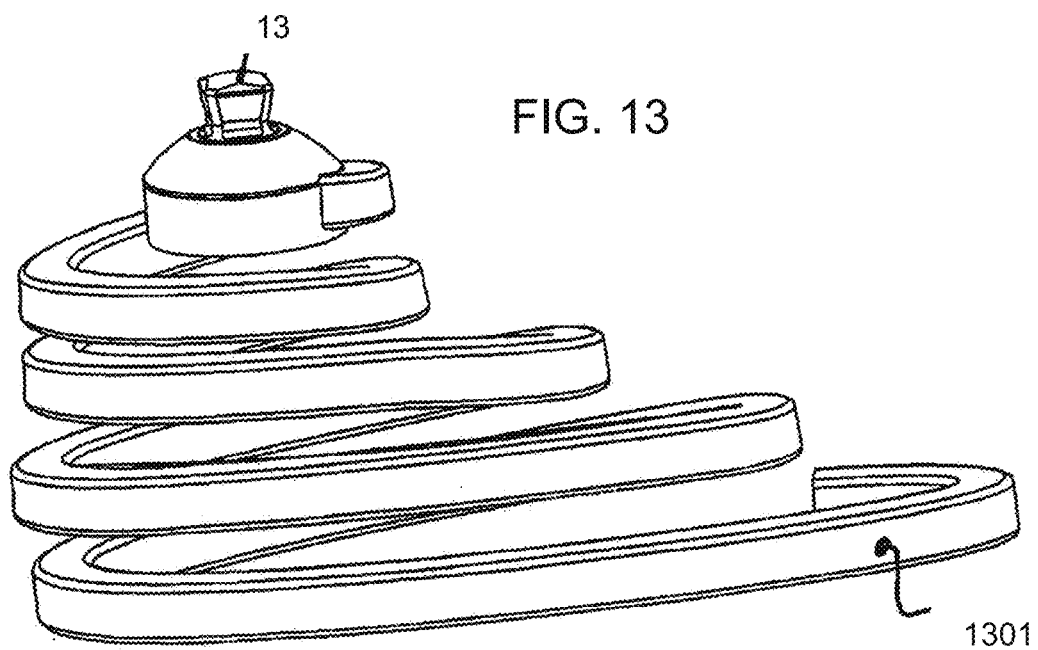
FIG. 13 illustrates a single coil foot design

Reference is now made to FIGS. 10 and 12. The composite members are preferably manufactured from materials containing long, commonly referred to as continuous, reinforcing fibers such as carbon, Kevlar, or fiberglass preimpregnated with curable resin, which are configured around an inflatable bladder or other device to form the core of the element, within a mold. Most commonly a bladder is used to apply the necessary laminate compaction pressure by being inflated and the mold is heated to a temperature sufficient to melt the resin and activate the curing process. This forms the composite fibers into a tubulous shape with a circular cross-section or other non-circular cross-sectional shape. This tubulous configuration permits the composite material to handle shear stresses very effectively. The result is a stiff tubular frame that is extraordinarily light. The diameter of the composite tube, the cross-sectional shape of the tube, the thickness and number of layers of composite material utilized and the composition of the composite materials utilized may be altered to achieve optimum performance characteristics.

Many variations are possible in the manufacturing process of hollow composite tubing. For example, disentegratable core material may be used inside an inflatable bladder to rigidize the bladder, making it easier to place fiber materials on the bladder. The entire assembly, consisting of fiber overwrapping the bladder with an internal core may then be placed inside the mold, the mold can then be closed and heated, and air or other gas is used to pressure the bladder internally, compacting and applying pressure to the fiber resin composite structure. In addition, fiber material may also be placed directly on the tool mold cavity surfaces. Some fiber material could be placed in the tool and some material placed on the bladder.

Pre-impregnated fiber material is generally used, which has uncured epoxy resin already impregnated into the fiber. Dry fiber can also be used, such as woven or braided material. If dry materials are used, liquid epoxy resin can be injected during cure using an external pump or a transfer device inside the tool which forces a volume of resin to be moved from a precharged reservoir in the tool into the part during cure. Inflation of the internal pressure bladder can be coordinated with the resin injection in this case.

A preferred construction of composite fiber tubing utilizes unidirectional fiber oriented along the wire sections, at 0°, consisting of roughly 25% to 75% of the total laminate thickness. Additional layers of fiber are oriented at ±45° and at 90° to the wire center line. The fibers may also be oriented at other angles corresponding to the principle directions of stress within the structure. The use of ±45° fiber in the hollow tubing wall allows the springs to efficiently store, release and carry torsional and transverse shear loads. Prior art dynamic response prosthetic feet produced in autoclaves lack this ability and their geometries are significantly restricted.

The use of ±45° and optionally 90° fiber orientation in the composite fiber tubing walls sections also greatly strengthens the resistance to delamination type forces. In sum, the use of hollow composite tubular walled wire sections containing ±45° and optionally 90° fiber in the cross section walls allows the spring to become a torsional spring in some or all areas rather than a pure flexural spring as in prior art dynamic response feet. The ability to carry torsional loads allows a more complex geometry, which in turn allows designs to be developed with longer wire lengths. This allows greater compliance in the foot while reducing or maintaining stresses at the previous level. This allows greater compliance while minimizing breakage and delamination problems. The use of hollow cross sections also removes inefficient material from the prosthetic foot, reducing the weight of the foot. If a wide flat cross section is desired, multiple hollow cavities extending the length of the section may be utilized in what is referred to as a multi-celled hollow structure.

It will also be understood that the hollow tubulous elements may be filled with various other materials as deemed necessary to enhance the performance of the foot.

A helical structure of the spring allows the efficient storage of torsional loads over a relatively long wire length. The cross section of the wire in the loops of the heel spring may also vary to alter the compression profile of the spring.

Apart from changing composition of composite materials utilized, such as utilizing fiberglass for lower modulus and higher flexibility in portions of the composite frame, the fiber orientation may also be changed to provide additional strength in certain directions. For instance, the fibers are preferably aligned at about a 45 degree angle to the axis of the tubing to manage the torsional load in the helical spring portions of the frame. By utilizing helical spring elements additional effective length is added to the springs while providing relatively lower profile for the dynamic responsiveness or energy sharing capacity of the foot.

Refer now to FIGS. 1 and 2. It illustrates a double coil design inside a cutaway view of a cosmesis. The three principle directions or axes of the foot geometry system are shown. Both coils have their primary axis oriented vertically. The aft coil is a tapered helix several coils long 103, while the forward coil 102 is only one coil long and constant taper. The primary axis of forward coil may alternatively be rotated 90 degrees to be oriented in the lateral axis. The foot is typically covered with a cosmesis 101, normally a flexible rubber with a color to match the amputee's skin color. The cosmesis typically provides the structural interface between the shoe and the internal foot structure. Sometimes additional foot plates are added to the bottom of the foot structure to interface structurally between the cosmesis and the foot structure. In this embodiment the forward coil and aft coils would be made separately, and joined together somewhere along the side piece 201. The upper square piece is typically titanium and connects to a standardized pyramid adapter connection to the rest of the prosthesis connected to the patient's residual limb. The upper connector piece 105 is made of aluminum in this embodiment and the carbon fiber members are bonded into receptacles provided in it.

Refer now to FIGS. 3 and 4. It illustrates a foot design with four separate lightly curved tubulous limbs inside a cutaway view of a cosmesis. This embodiment illustrates a foot design much simpler geometrically than the double coil design shown in FIGS. 1 and 2. However, the most of the advantages of the hollow tubulous member feet of the present invention are still obtained. Four receptacles 307, 401 are provided in the upper connector piece 302 for connecting to the four hollow tubes 303, 304, 305, 306. Sometime the hollow spaces in the tube might be filled with epoxy or other material to enhance various characteristics.

Figure 11:
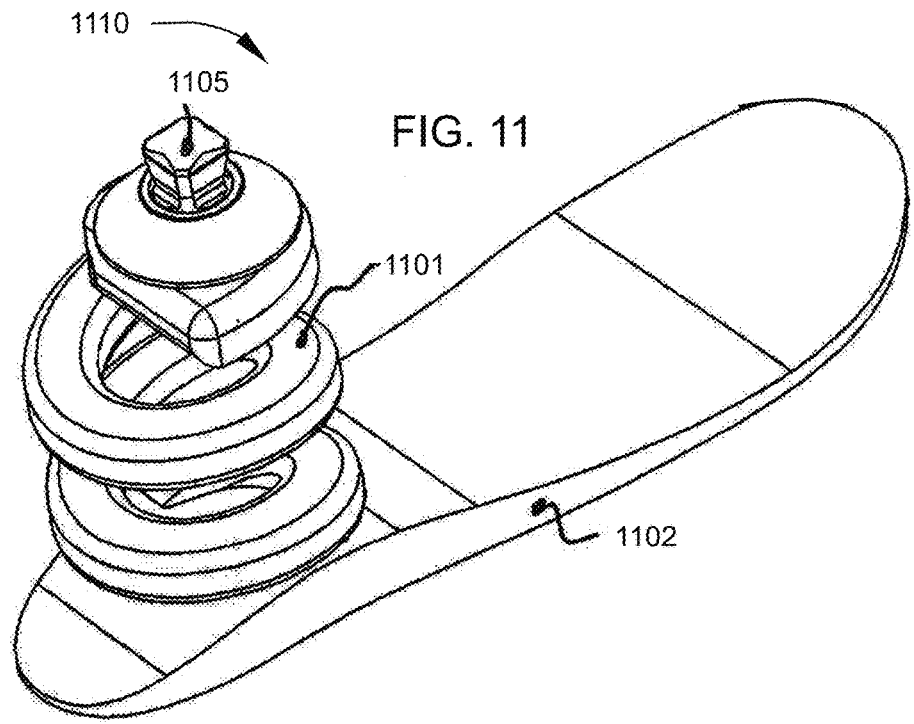
FIG. 11 illustrates a single coil foot design

Refer now to FIGS. 5 and 11. They illustrate the use of straight helical tubulous composite members 501, 502, 1101; and a separately formed base plate 501, 1102. The base plates could be either a flat solid composite laminate, or a hollow partially tubular structure. Foot 510 in FIG. 5 uses two coils 501, 502 which are nested inside each other. Foot 1110 uses only one coil member 1101.

Figure 9:
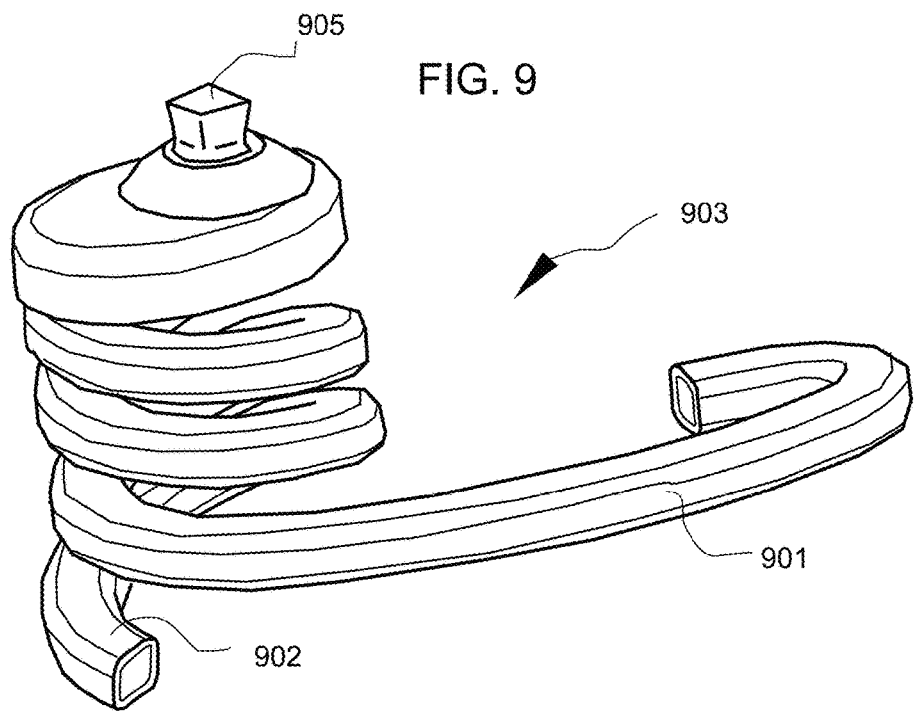
FIG. 9 illustrates a nested double coil foot design

Refer now to FIGS. 9, 10 and 12. FIG. 9 illustrates a foot 903 constructed with two separately molded tubulous members 901, 902. The heel member 902 is a straight helical path, while the forward member 901 is a helical path integrated with a toe section. FIG. 10 illustrates the molding tooling 1010 used for manufacturing the forward member 901. The external molding tooling 1001 and 1002 contain and enclose all the mold components and have surfaces which form about half of the external surface of forward member 901. There are several internal mold components which fit inside the mold 1003, 1004, 1005, 1006, 1008 and form the other approximately half of the external surface of the forward member 901. There is also an internal core piece 1007 which facilitates removal of the internal mold components from the molded forward member 901. Likewise, FIG. 12 illustrates the molding tooling 1210 used for manufacturing the heel member 902. The external molding tooling 1201 and 1202 contain and enclose all the mold components and have surfaces which form about half of the external surface of heel member 902. There are several internal mold components which fit inside the mold 1203, 1204, 1205 1207 and form the other approximately half of the external surface of the heel member 902. There is also an internal core piece 1207 which facilitates removal of the internal mold components from the molded heel member 902.

Figure 6:
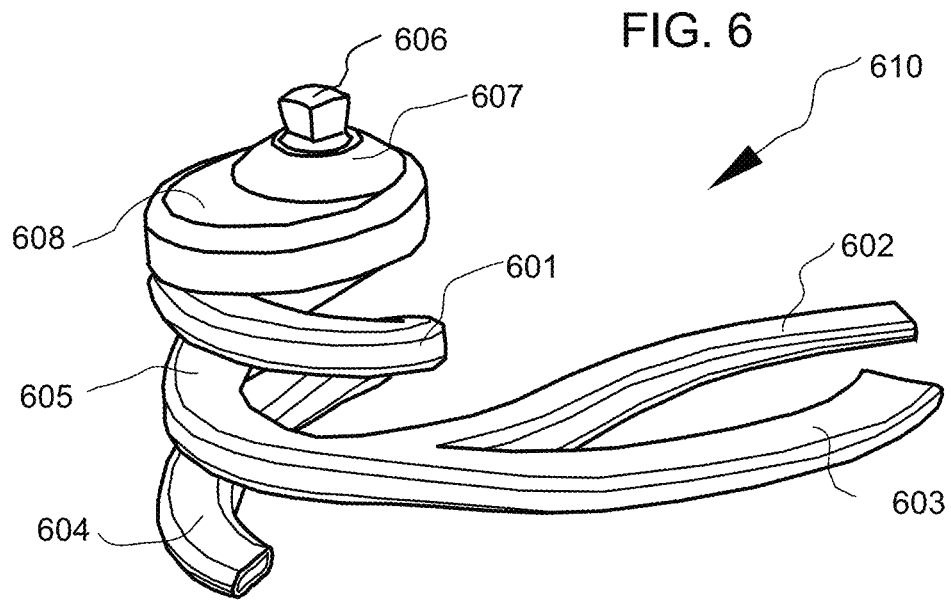
FIG. 6 illustrates a nested double coil foot design

Refer now to FIG. 6. Foot 610 illustrates the use of tubulous composite member 605 that bifurcates into two separate members 602 and 603 to form toe pieces for the forward section. This foot 610 also uses a nested coil for the aft heel member 601.

Figure 14:
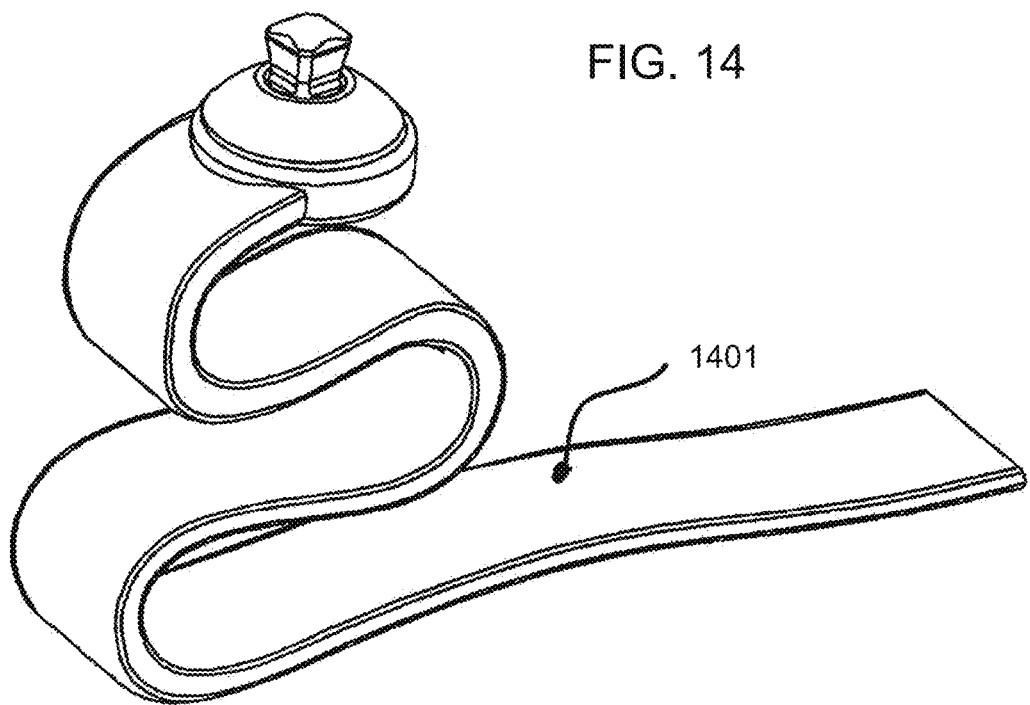
FIG. 14 illustrates sulcated tubulous member
Figure 19:
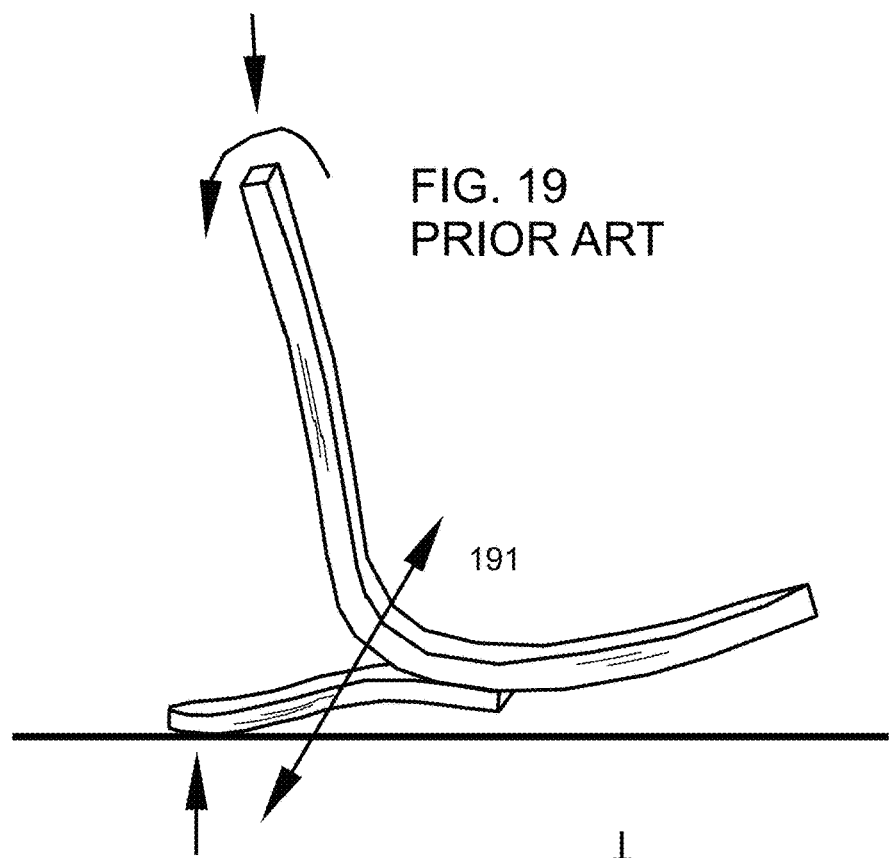
FIG. 19 is a schematic illustrating a prior-art prosthetic foot construction.
Figure 20:
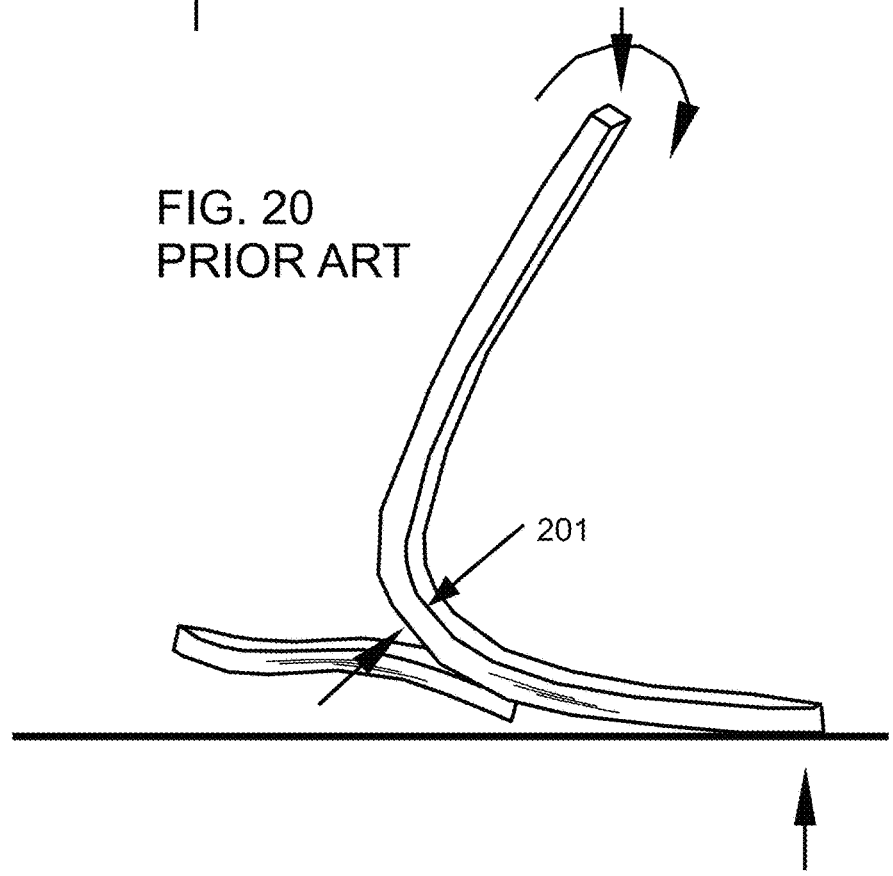
FIG. 20 is a schematic illustrating a prior-art prosthetic foot construction.

Refer now to FIG. 14 which illustrates a tubulous composite member 1401 which is very thin and wide and traces a fairly long sulcated path. This member illustrates the range of cross sections contemplated by the present invention. This single cavity inside this particular tubulous member, a lumen, might be replaced with several lumens to aid shear transfer from the upper to lower surfaces.

Figure 22:
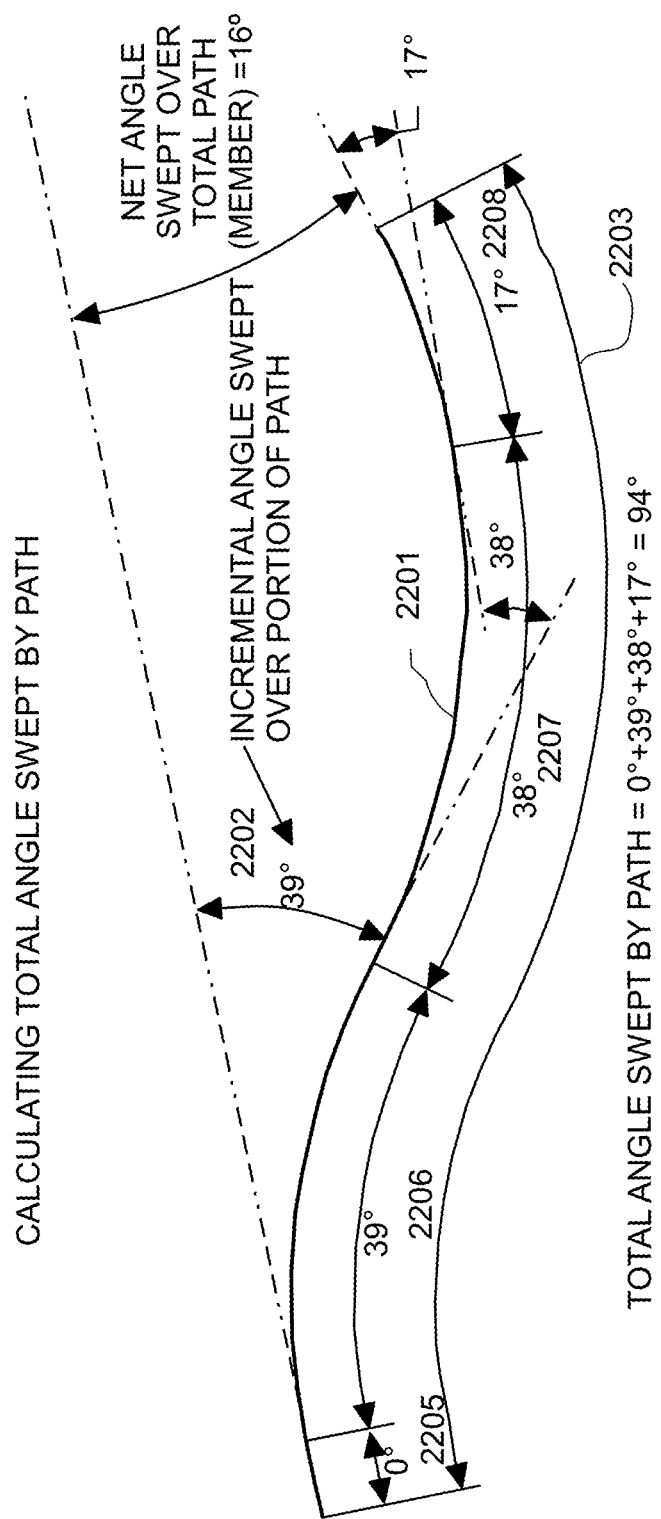
FIG. 22 illustrates the method for measuring the angular sweep of longitudinal centerline path of a tubulous member.
Figure 23:
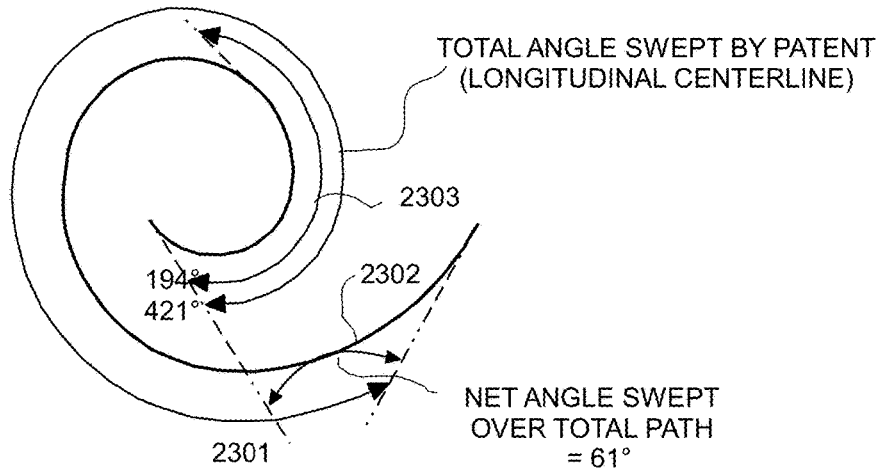
FIG. 23 illustrates the method for measuring the angular sweep of longitudinal centerline path of a tubulous member.
Figure 24:
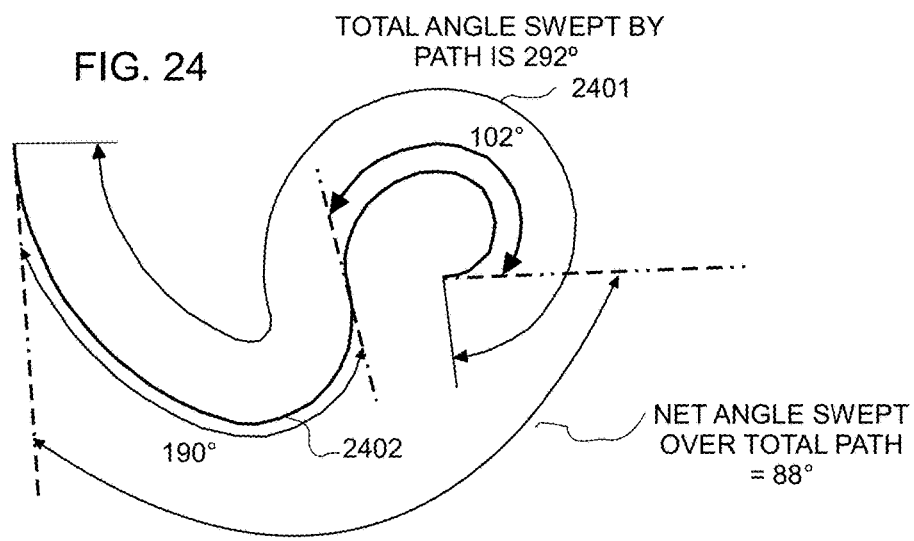
FIG. 24 illustrates the method for measuring the angular sweep of longitudinal centerline path of a tubulous member.

Refer now to FIGS. 21-24. These illustrate the various ways of measuring the amount of curving in a particular tubulous composite member. As noted above in the description of FIGS. 1 and 2, the range of geometries and complexity of the geometric shapes that individual tubulous members can have as described in the present invention can vary widely from the members 102, 103, 201 of the complex geometry of foot 100 in FIGS. 1 and 2; to the relatively simpler geometries of the members 303, 304, 305, 306 of foot 300 in FIGS. 3 and 4. The wide and thin tubulous member of FIG. 14 also illustrates this range of geometries. The amount of and type of curves in these various members, which are all part of the present invention, can be described with several parameters. All these measurements and descriptions pertain to the centerline along the longitudinal lengthwise path of the tubulous member. These measurements also refer to values calculated from projections of the paths onto one of the three primary planes. The three following angular measurements have been used and are expressed in degrees arc:

The "Total Angle Swept by Path" 2202, 2301, 2401 illustrated. In the case of FIG. 22, this is a sum of all the angular changes 2205, 2206, 2207, 2208 swept by the path and is always greater than zero, or equal to zero only in the case of a straight tube.

The "Incremental Angle Swept over portion of path" 2205, 2206, 2207, 2208 is also shown in FIG. 22. Each of these separately is a positive value.

The "Net Angle Swept over total path" for the member is the angular misalignment of between the beginning of a member and the end of a member as projected onto a principle plane.

Other generic descriptors of these geometric paths include:

The shape of the path may be "fully three dimensional" which implies that it has significant curvatures in two separate principle planes. A path shape with all curves constrained to one principle plane would not be "fully three dimensional".

Path shapes with "reverse curves" are those where the centerline first curves in one direction and then at some later point curves significantly in the opposition direction.

All publications, patents, and patent documents are incorporated by reference herein as though individually incorporated by reference. Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

What is claimed is:

1. A prosthetic foot comprising:
a single continuous molded carbon fiber composite member with an elongated shape extending along a path of a hollow heel spring portion and a hollow forward spring portion joined to form the single continuous molded carbon fiber composite member with each portion comprising fibers arranged along the path of the member to provide bending strength and stiffness and bias oriented fibers extending around an entire circumference of the composite member to provide torsional strength to store, release and carry torsional and transverse shear loads;
a mounting element for securing the prosthetic foot to a lower limb prosthetic structure,
the hollow heel spring portion configured as a tubulous hollow molded carbon fiber coil having a path that includes a helical path around a heel spring axis,
the helical path with at least one complete 360 degree coil around the heel spring axis, the heel coil spring portion attached to the mounting element with the heel spring axis extending vertically downward
the hollow forward spring portion configured as a tubulous hollow molded carbon fiber coil attached to and extending forward from the mounting element in a path that includes a helical path portion around a forward spring axis,
the helical path portion having at least one complete 360 degree coil around the forward spring axis.

2. The prosthetic foot of claim 1 wherein the hollow heel spring portion is configured as a tubulous hollow molded carbon fiber coil having a path that includes a helical path around a heel spring axis, the helical path with at least three complete 360 degree coil around the heel spring axis.

3. The prosthetic foot of claim 1 wherein the fibers in the heel spring portion are arranged in at least two plies that have different angular orientations with respect to the path of the heel coil spring portion.

4. The prosthetic foot of claim 3 wherein the angular orientation of fibers in any ply of the at least two plies is a nominal degree angle of +45 degrees, −45 degrees, 90 degrees or 0 degrees with respect to the path of the heel coil spring portion.

5. The prosthetic foot of claim 1 wherein the forward spring axis of the helical path portion of the forward coil spring extends vertically.

6. The prosthetic foot of claim 1 wherein the forward spring axis of the helical path portion of the forward coil spring extends laterally.

7. The prosthetic foot of claim 1 wherein the forward coil spring includes an integrated toe section.

8. The prosthetic foot of claim 1 wherein the fibers in the forward spring portion are arranged in at least two plies that have different angular orientations with respect to the path the forward coil spring portion.

9. The prosthetic foot of claim 8 wherein the angular orientation of fibers in any ply of the at least two plies is a nominal degree angle of +45 degrees, −45 degrees, 90 degrees or 0 degrees with respect to the path of the forward spring portion.

* * * * *